(12) United States Patent
Turcott

(10) Patent No.: US 6,561,984 B1
(45) Date of Patent: May 13, 2003

(54) ASSESSING HEART FAILURE STATUS USING MORPHOLOGY OF A SIGNAL REPRESENTATIVE OF ARTERIAL PULSE PRESSURE

(75) Inventor: Robert Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/981,591

(22) Filed: Oct. 16, 2001

(51) Int. Cl.[7] .................................. A61B 5/00

(52) U.S. Cl. .................. 600/485; 600/500; 600/480

(58) Field of Search ..................... 600/485, 490, 600/493–6, 500, 503, 504–7, 526, 476–480

(56) References Cited

U.S. PATENT DOCUMENTS

| | | | | |
|---|---|---|---|---|
| 5,241,966 A | * | 9/1993 | Finkelstein et al. | 600/526 |
| 5,634,467 A | * | 6/1997 | Nevo | 600/500 |
| 5,730,137 A | * | 3/1998 | Amano et al. | 600/500 |
| 5,913,826 A | * | 6/1999 | Blank | 600/500 |
| 6,117,087 A | * | 9/2000 | Kamm et al. | 600/504 |
| 6,336,903 B1 | * | 1/2002 | Bardy | 600/508 |

* cited by examiner

Primary Examiner—Robert L. Nasser
(74) Attorney, Agent, or Firm—Steven M. Mitchell

(57) ABSTRACT

The heart failure (HF) status of a patient is determined based on the frequency characteristics of a signal representative of arterial pulse pressure. The signal can be a plethysmography signal that is produced by a implantable sensor or a non-implanted sensor. The signal can be produced by a chronically implantable sensor.

10 Claims, 17 Drawing Sheets

ASSESSING HEART FAILURE STATUS USING MORPHOLOGY OF A SIGNAL REPRESENTATIVE OF ARTERIAL PULSE PRESSURE

This application is related to copending application Ser. No. 09/981,570, filed on Oct. 16, 2001.

BACKGROUND OF THE INVENTION

1. Field of the Invention

The present invention relates generally to non-invasive and implantable (i.e., invasive) methods, devices and system for assessing heart failure status using morphology of a signal representative of arterial pulse pressure. Specific embodiments of the present invention relate to assessing heart failure status based on the morphology of a plethysmography signal.

2. Related Art

Heart failure (HF) is a pathophysiologic state in which an abnormality of myocardial function inhibits the ventricles from delivering adequate quantities of blood to metabolizing tissues at rest or during activity. It results not only from a decrease in intrinsic systolic contractility and/or diastolic relaxation of the myocardium but also from alterations in the pulmonary and peripheral circulations as well. HF can develop from a variety of different causes. Coronary artery disease, hypertension, and idiopathic cardiomyopathy are common risk factors for HF. Acute conditions that may result in HF include acute myocardial infarction (AMI), arrhythmias, pulmonary embolism, sepsis, and acute myocardial ischemia. Gradual development of HF may be caused by liver or renal disease, primary cardiomyopathy, cardiac valve disease, anemia, bacterial endocarditis, viral myocarditis, thyrotoxicosis, chemotherapy, excessive dietary sodium intake, and ethanol abuse. Drugs can also worsen HF. Drugs that may cause fluid retention, such as nonsteroidal anti-inflammatory drugs (NSAIDs), steroids, hormones, antihypertensives (e.g., hydralazine, nifedipine), sodium-containing drugs (e.g., carbenicillin disodium), and lithium may cause congestion. Beta blockers, antiarrhythmics (e.g., disopyramide, flecainide, amiodarone, sotalol), tricyclic antidepressants, and certain calcium channel blockers (e.g., diltiazem, nifedipine, verapamil) have negative inotropic effects and further decrease contractility in an already depressed heart. Direct cardiac toxins (e.g., amphetamines, cocaine, daunomycin, doxorubicin, ethanol) also can worsen or induce HF.

When the heart fails as a pump and cardiac output (the volume of blood pumped out of the ventricle per unit of time) decreases, a complex scheme of compensatory mechanisms to raise and maintain perfusion to vital organs. These compensatory mechanisms include increased preload (volume and pressure or myocardial fiber length of the ventricle prior to contraction, i.e., end of diastole), increased afterload (vascular resistance), ventricular hypertrophy (increased muscle mass) and dilatation, activation of the sympathetic nervous system (SNS), and activation of the renin-angiotensin-aldosterone (RAA) system.

Although initially beneficial for maintaining perfusion, these compensatory mechanisms are ultimately associated with further pump dysfunction. In effect, the consequence of activating the compensatory systems is a worsening of the HF. This is often referred to as the "vicious cycle of HF". Without therapeutic intervention, some of the compensatory mechanisms continue to be activated, ultimately resulting in a reduced cardiac output and a worsening of the patient's HF symptoms. It becomes apparent why one goal in the treatment of HF is to interrupt this vicious cycle as soon as possible. Accordingly, there is a need for detecting HF as early as possible.

Prior attempts to detect HF symptoms require a large amount of interaction by the patient. For example, U.S. Pat. No. 6,080,106 (Lloyd, et al.) describes a patient interface system with a scale. The patient interface system described in the '106 patent includes a patient data input means having both a scale and a question and answer means. The question and answer means presents the patient with one or more questions related to the patient's health status and records the patient's answers to the questions. Example questions include: (1) "Were you tired during the day?"; (2) "On a scale of 1 to 5, 5 being most, how tired were you in the middle of the day?"; (3) "Did you cough during the night?"; (4) "Did you need an extra pillow to sleep?"; (5) "Are your shoes tighter than usual?"; (6) "Did you exercise today?"; and the like. In operation, the patient steps onto a scale, which automatically activates a processor that compares the weight measured by the scale with the minimum and maximum weights stored in a memory. The measured weight and deviation (if any) from the target weight is displayed on a visual display, and is stored for later transmission to a monitoring staff. The question and answer means then presents questions selected by the patient's physician, designed to elicit details about the patient's condition. The patient responds by pressing a button that corresponds to the desired answer, or, optionally, the patient simply speaks his or her responses into microphone. Once the series of questions and answers is completed, a processor transmits the measured data and patient's answers to the monitoring staff via modem. While connected to the monitoring staff's computer, the answers and data are examined by the monitoring staff (or compared immediately by the monitoring staff s computer), and new questions, target values, and minimum/maximum values are downloaded to the processor. In this manner, cardiac associated diseases, such as HF, can be remotely monitored. A problem with the system of the '106 patent is that it requires a large amount of interaction by the patient. Minimally, the system requires that the patient step on a scale and answer one or more questions. This requires that the patient has the time and the initiative to performs these steps. This also requires that the patient remembers to perform these steps. Additionally, such questions and answers are very subjective, resulting in a very subjective monitoring of HF.

Some of these limitations have been addressed by the development of an implantable system that monitors hemodynamic status (Medtronic Chronicle, Medtronic, Inc., Minneapolis, Minn.). While this system potentially avoids the need for active patient participation, it relies on an intravascular sensor placed in the right ventricle of the heart. This approach is consistent with the prior art for implantable hemodynamic status monitoring, which has to date focused on intravascular or intramyocardial instrumentation. Examples include U.S. Pat. No. 5,454,838 in which Vallana et al. teach placement of a sensor on the myocardial wall using an intravascular approach. In U.S. Pat. No. 5,496,351, Plicchi et al. propose placing a sensor within the myocardial wall. Mortazavi in U.S. Pat. No. 5,040,538 and Cohen et al. in U.S. Pat. No. 4,815,469 describe placement of an optical sensor within the right ventricle. In the context of hemodynamic assessment for arrhythmia discrimination, Cohen and Liem (Circ., 1990, 82:394–406) study the effectiveness of a pressure transducer placed in the right ventricle. Clearly, powerful information about hemodynamic status can be obtained using intravascular instrumentation. However, intravascular or intramyocardial instrumentation carries significant risks to the patient, including increased perioperative morbidity and mortality, and increased long-term risks such as stroke and pulmonary embolism. Furthermore, intravascular instrumentation can only be performed by extensively trained specialists, thereby limiting the availability of qualified physicians capable of implanting the device, and increasing the cost of the procedure. Finally, because of the added patient risks and greater physical demands of an intravascular environment, the intravascular placement of the sensor increases the cost of development, manufacturing, clinical trials, and regulatory approval.

There is a need for methods, devices and systems that can access the HF status of patients with minimal or no interaction by the patient. Preferably, such methods, devices and systems do not rely on subjective information. Further, it would be beneficial if such methods, devices and systems can be as inexpensive and safe as possible. It would also be beneficial if such methods, devices and systems can be implemented into methods, devices and systems that are already used to monitor the heart for other reasons. In addition, to reduce cost and increase safety, it would be desirable to use monitoring methods and devices that do not require intravascular instrumentation.

SUMMARY OF THE INVENTION

The present invention is directed to methods for assessing heart failure (HF) status, and monitoring devices and systems that assess HF status. More specifically, the present invention relates to assessing HF status based on morphology of a signal representative of arterial pulse pressure. Specific embodiments of the present invention relate to assessing heart failure status based on the morphology of a plethysmography signal.

An embodiment of the present invention includes producing a plethysmography signal that is representative of arterial pulse pressure. HF status is then assessed based on the frequency characteristics of the plethysmography signal. Each cardiac cycle of the plethysmography signal includes a primary pulse, a secondary pulse, and a dicrotic notch that separates the primary and secondary pulses. The height of and area under these pulses change when a HF exacerbation is developing. This enables HF assessment to be based on the frequency characteristics of a plethysmography signal.

The plethysmography signal can be produced by transmitting light from a light source (e.g., toward a capillary bed) and receiving a portion of the light transmitted from the light source at a light detector. The portion of light received at the light detector has an associated detected light intensity that is directly representative of blood volume, which is indirectly representative of the arterial pulse pressure. The plethysmography signal is then produced based on the received portion of light. The light source and the light detector can be arranged in a transmission or reflection configuration.

In an alternative embodiment, the plethysmography signal is produced by transmitting light from a light source (e.g., toward a capillary bed), wherein an intensity of the transmitted light is based on a light control signal. A portion of the transmitted light is then received at a light detector, the received portion having an associated detected light intensity. A feedback signal is produced based on the received portion of light, wherein the feedback signal is indicative of the detected light intensity. The feedback signal is then compared to a reference signal to produce a comparison signal, which is used to adjust the light control signal. The plethysmography signal is then produced based on the comparison signal and/or the light control signal.

According to an embodiment of the present invention, an alert indicator is triggered based on the shape of the plethysmography signal.

In an embodiment of the present invention, a chronically implantable sensor is used to produce a signal that is representative of arterial pulse pressure. HF status is then assessed based on the frequency characteristics of the signal that is representative of arterial pulse pressure. The chronically implantable sensor can be an extravascular sensor that includes a light source and a light detector, and the signal can be a plethysmography signal. Alternatively, the chronically implantable sensor can be a intra-arterial sensor, such as a pressure sensor. The intra-arterial sensor should be implanted in an appropriate location, such as the pulmonary artery, so that a signal including the desired dicrotic characteristics is produced. The values mentioned above can be determined based on the signal produced using the chronically implanted sensor. HF status can then be assessed based on these values.

BRIEF DESCRIPTION OF THE FIGURES

Further features and advantages of the present invention may be more readily understood by reference to the following description taken in conjunction with the accompanying drawings. The left-most digit(s) of a reference number identifies the drawing in which the reference number first appears.

DETAILED DESCRIPTION OF THE INVENTION

Figure 1:
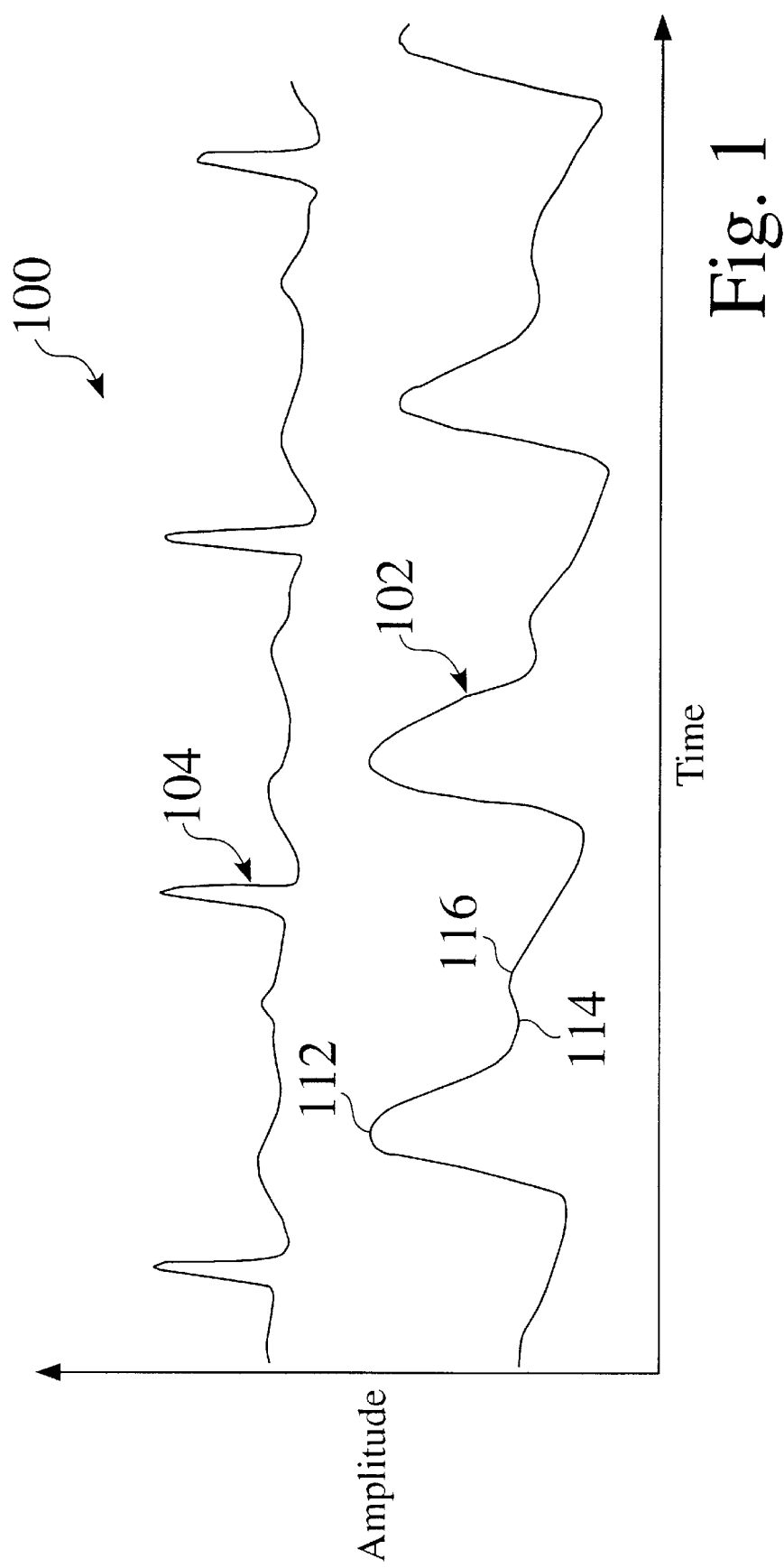
FIG. 1 illustrates exemplary plethysmography and electrocardiogram signals.

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

I. Overview of Present Invention

At least one study has suggested that observations of arterial pulse pressure waveforms can be used to assess severe functional impairment of the myocardium. See Ewy et al., "The Dicrotic Arterial Pulse," *Circulation*, Volume XXXIX (May 1969), which is incorporated herein by reference. In the Ewy et al. article, arterial pulse pressure was measured based on indirect recordings from the carotid artery (on the neck of a patient) and direct recordings of the brachial artery (on the arm of a patient). Indirect recordings from the carotid artery requires holding a transducer against the neck of the patient, and is thus, not practical for chronic HF status assessment. Direct recordings of the brachial artery requires the temporary insertion of a transducer into the arm of a patient, and thus, is also not practical for chronic HF status assessment. Specific embodiments of the present invention overcome these disadvantages of the Ewy et al. article by providing for chronic assessment of HF status. Other embodiments improve upon the HF status assessment process introduced in the Ewy et al. article.

II. Plethysmography Morphology

According to an embodiment of the present invention, a plethysmography device is used to produce a signal representative of arterial pulse pressure. Stated another way, this embodiment of the present invention uses plethysmography morphology in the assessment of HF status. This is advantageous for many reasons, some of which are discussed below.

First, if an HF monitor is implemented as a chronically implantable device, a plethysmography signal can be produced using an extravascular sensor (as will be described below). An extravascular sensor is much easier, quicker and less expensive to install than more invasive sensors, such as an intra-arterial sensor or a sensor placed in a heart chamber such as the right ventricle or right atrium. Because an extravascular sensor is relatively noninvasive, it is safer than a more invasive sensor (e.g., an intravascular sensor). Additionally, the engineering requirements of an extravascular sensor are much less demanding than the requirements of more invasive sensors that are constantly exposed to the blood stream. Furthermore, an extravascular sensor can typically be implanted by a general cardiologist. In contrast, a more invasive sensor would typically require a more specialized electrophysiologist for installation.

If an HF monitor is implemented as a non-implantable device, a plethysmography signal can be produced using a device that easily clips on a finger, toe or earlobe, as will be explained in more detail below. Thus, patients are likely to tolerate regular use of these devices for an extended period of time, such as during sleep each night. Particularly convenient embodiments include a finger cuff, a wristband, a configuration resembling a watch, and a configuration resembling a clip-on earring.

The term "plethysmography" is a generic term referring to a variety of techniques for monitoring volume changes. As used herein, the term "plethysmography" refers to techniques for monitoring volume changes in blood vessels of a limb or tissue segment. The term "morphology" refers to the shape of a waveform or portion thereof Thus, the term "plethysmography morphology" herein refers to the shape of a waveform representing volume changes in blood vessels.

Volume changes in blood vessels occur in a pulsatile manner with each beat of the heart as blood flows in and out of a portion of the body. A plethysmography device produces waveform measurements that are similar to arterial pressure waveform measurements, because changes in arterial pressure correspond to relative changes in blood volume. Plethysmography waveforms have typically been used for measuring pulse velocity and indicating arterial obstructions. In contrast, the present invention uses plethysmography waveforms to assess HF status. The Ewy et al. article did not teach or suggest using plethysmography morphology to assess HF status.

FIG. 1 illustrates an exemplary plethysmograph 100, which includes a plethysmography waveform 102 of a normal subject produced by a plethysmography device. For timing reference, an electrocardiogram (ECG) signal 104 is illustrated. Waveform 102 provides a measure of the volume of the arterial vasculature. A measure of arterial pulse amplitude is derived from it. A few tens to a few hundreds of milliseconds after the QRS complex, the plethysmography amplitude reaches a minimum and starts to increase. This is due to the increasing blood volume in the arterioles as the systolic pulse reaches the periphery. The delay is influenced by the distance that the sensor is placed from the heart. It requires approximately 100 msec for the amplitude of the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

One type of plethysmography device is a photoplethysmography device (PPG) (also called a pseudoplethysmography or photoelectric plethysmography device), which includes a light detector and a light source. The photoplethysmography utilizes the transmission or reflection of light to dermonstrate the changes in blood perfusion. Such devices are typically used in the cardiology department or intensive care department of a hospital or in a clinic for diagnostic purposes related to vascular surgery. All such photoplethysmography devices are referred to, herein, simply as plethysmography devices.

A. Exemplary Plethysmography Devices

Figure 2A:
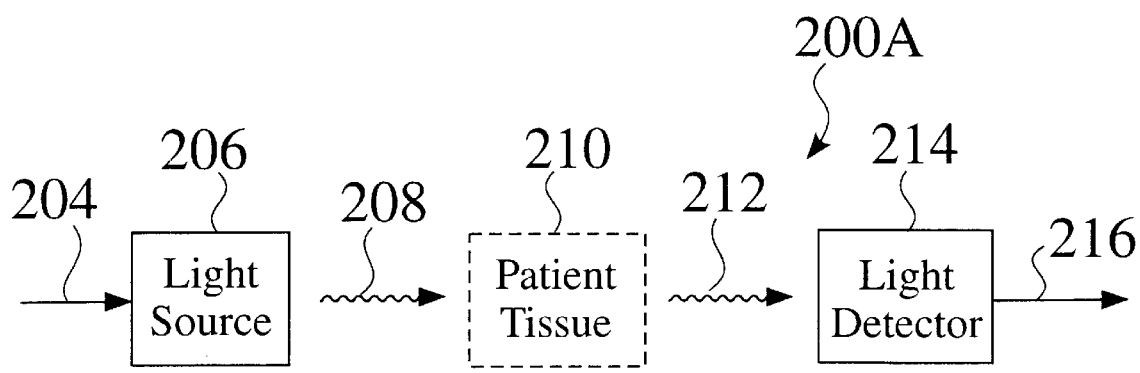
FIG. 2A is a block diagram illustrating an exemplary conventional photoplethysmography device.
Figure 2B:
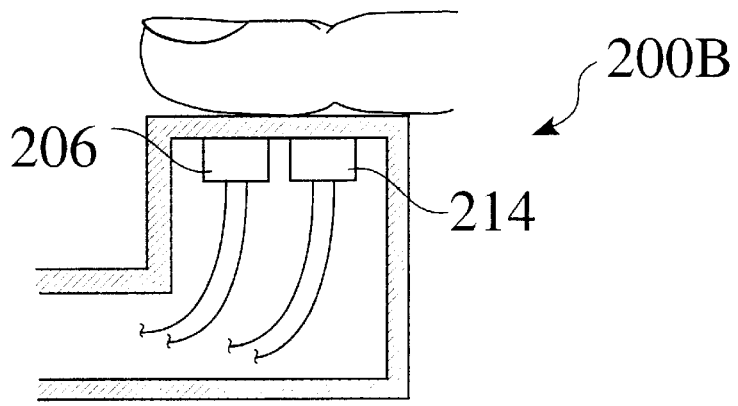
FIG. 2B is a simplified mechanical diagram illustrating a portion of an exemplary photoplethysmography device.
Figure 2C:
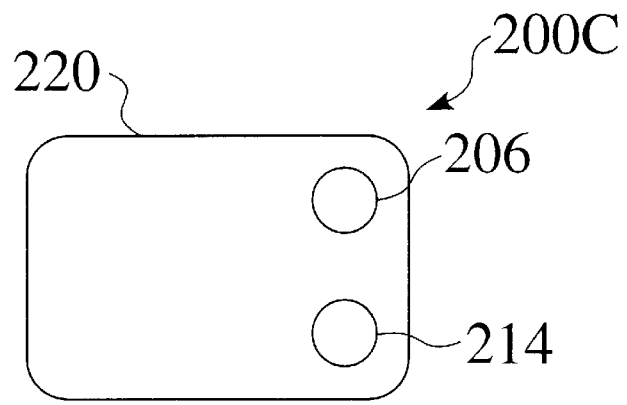
FIG. 2C is a simplified mechanical diagram illustrating an exemplary implantable photoplethysmography device.

A block diagram 200A of an exemplary photoplethysmography device is shown in FIG. 2A. An exemplary mechanical arrangement 200B for a noninvasive (i.e., not implanted) photoplethysmography device is shown in FIG. 2B. An exemplary mechanical arrangement 200C for a chronically implantable photoplethysmography device is shown in FIG. 2C.

The photoplethysmography device includes a light source 206 and a light detector 214. In one example, the light source 206 is a light-emitting diode (LED), although in alternative models an incandescent lamp or laser diode can be used as the light source. Referring to FIG. 2A, light source 206 outputs a transmit light signal 208 that is transmitted through and/or reflected by (depending on the embodiment) patient tissue 210. A receive light signal 212 is received by light detector 214. Light detector 214 can include, for example, a photoresistor excited by a constant current source. Changes in light intensity cause proportional changes in the resistance of the photoresistor. Since the current through the photoresistor is constant in this example, the resistance changes produce a varying analog voltage light detection signal 216. This varying analog voltage light detection signal 216, which is a plethysmography signal, is typically filtered and amplified and then converted to a digital signal using an analog to digital converter (not shown). The light detector can, for example, alternatively include a photodiode, phototransistor, photodarlington or avalanche photodiode. Light detectors are often also referred to as photodetectors or photocells.

Light may be transmitted through a capillary bed such as in an earlobe or finger tip. As arterial pulsations fill the capillary bed and pre-capillary arterioles, the changes in volume of the blood vessels modify the absorption, reflection and scattering of the light. Stated another way, an arterial pulse in, for example, a finger tip, or earlobe, causes blood volume to change, thereby changing the optical density of the tissue. Therefore, the arterial pulse modulates the intensity of the light passing through the tissue.

Photoplethysmography devices may operate in either a transmission configuration or a reflection configuration. In the transmission configuration, light source 206 and light detector 214 face one another and a segment of the body (e.g., a finger or earlobe) is interposed between source 206 and detector 214. In the reflection configuration, light source 206 and light detector 214 are mounted adjacent to one another, e.g., on the surface of the body, as shown in FIG. 2B. In this configuration, a fraction of light from light source 206 is backscattered by the tissue into light detector 214.

Referring to FIG. 2C, if the photoplethysmography device is incorporated into a chronically implantable device 220 (e.g., an implantable cardioverter defibrillator (ICD), pacemaker, or any other implantable device), light source 206 and light detector 214 can be mounted adjacent to one another on the housing or header of the implantable device. Light source 206 and light detector 214 are preferably placed on the side of implantable device 220 that, following implantation, faces the chest wall, and are configured such that light cannot pass directly from the source to the detector. Thus, the reflection configuration is preferably used when the plethysmography device is implemented in an implantable device. The placement on the side of device 220 that faces the chest wall maximizes the signal to noise ratio by 1) directing the signal toward the highly vascularized musculature, and 2) shielding the source and detector from ambient light that enters the body through the skin. Alternatively, at the risk of increasing susceptibility to ambient light, light source 206 and light detector 214 can be placed on the face of the device that faces the skin of the patient. Additional details of an implantable photoplethysmography device are disclosed in U.S. patent application Ser. No. 09/543,214, entitled "Extravascular Hemodynamic Sensor" (Turcott), filed Apr. 5, 2000, which is incorporated herein by reference.

Figure 3B:
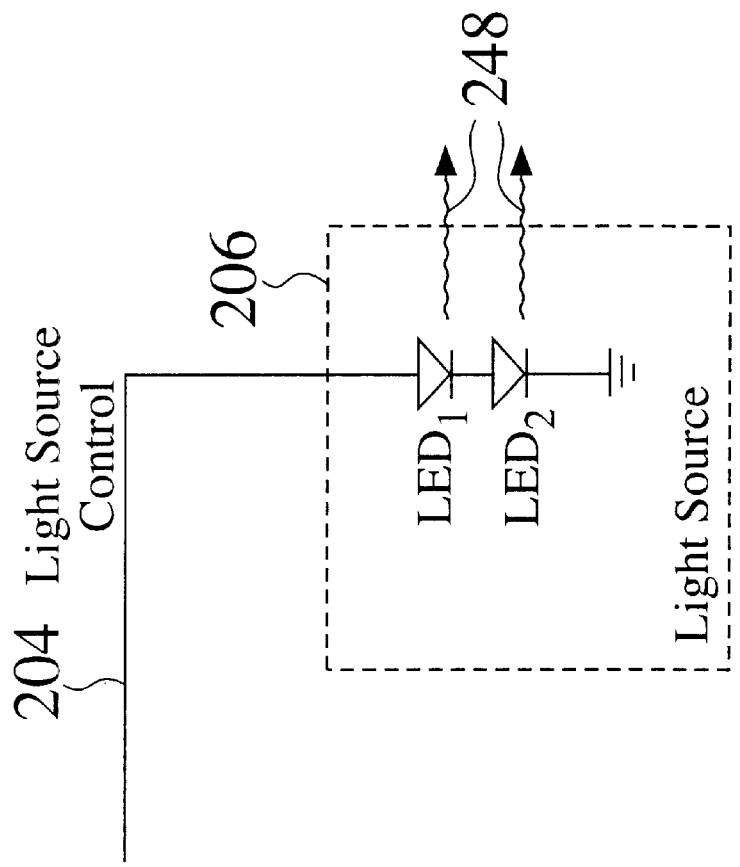
FIGS. 3A and 3B illustrate exemplary light sources for use in embodiments of the present invention.
Figure 3A:
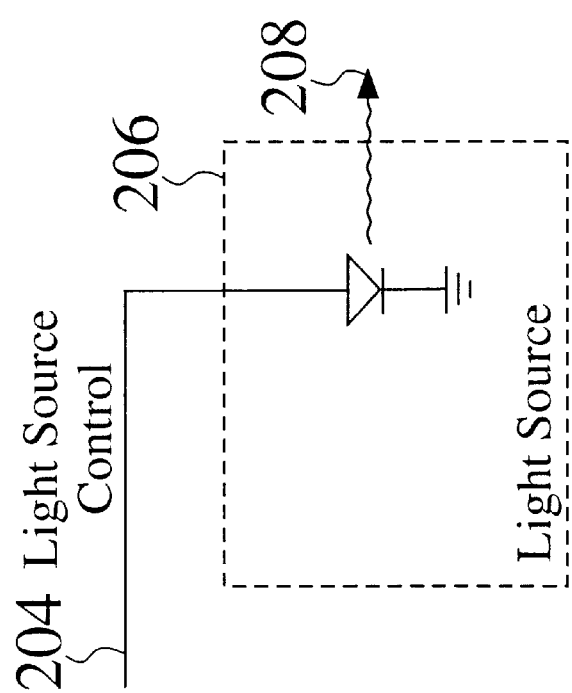

FIGS. 3A and 3B illustrate exemplary light sources for use in the embodiments of the present invention. Referring first to FIG. 3A, exemplary light source 206 includes a single LED that produces light signal 208. The LED can be, for example, a model L53SRC/F red LED, or a model L53F3C infrared LED, both manufactured by Kingbright Corporation, City of Industry, Calif. Referring to FIG. 3B, a series of LEDs (e.g., $LED_1$ and $LED_2$) can be used to increase the amount of optical power in light signal 208. Separate LEDs can be used. Alternatively, dual emitter combination LEDs can be used, such as model DLED-660/ 905-LL5-2, manufactured by UDT Sensors, Inc., Hawthorne, Calif. Light source 206 can be driven by a light control signal 204, as shown in FIGS. 2A, 3A and 3B. In a conventional plethysmography device, transmit light signal 208 would have a relatively constant average light intensity, though the light may be pulsed rapidly. Accordingly, in a conventional plethysmography device, light control signal 204 is relatively constant when averaged over a period of the pulse train.

One of ordinary skill in the art will appreciate that the use of other LEDs and other light sources (e.g., a laser diode) are within the spirit and scope of the present invention. Depending on the embodiment, light source 206 may or may not include additional elements that are used, for example, to maintain a relatively constant current through an LED.

Figure 4:
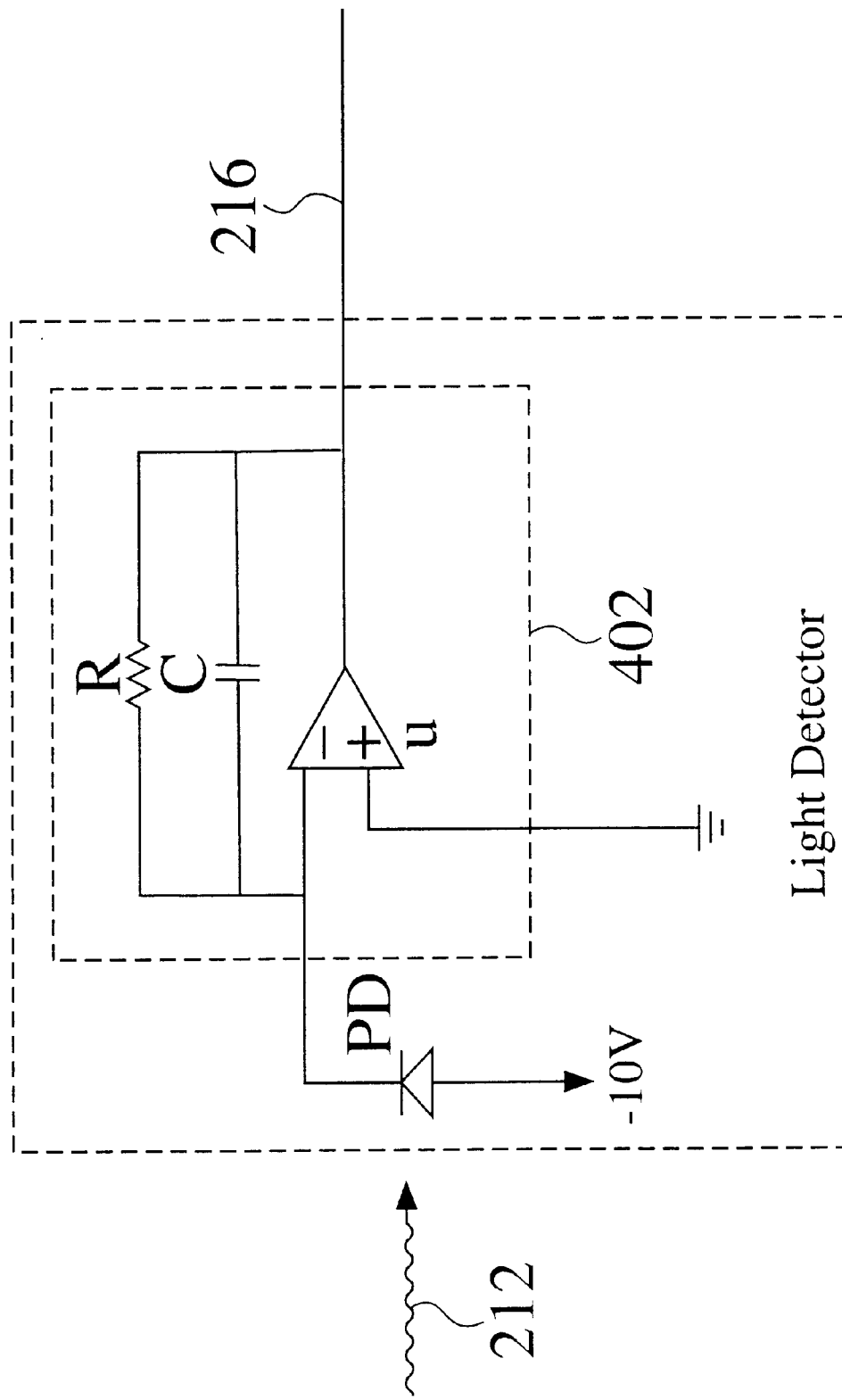
FIG. 4 illustrates an exemplary light detector for use in embodiments of the present invention.

FIG. 4 illustrates an exemplary light detector for use in embodiments of the present invention. Referring to FIG. 4, exemplary light detector 214 includes a photodiode PD operated in a current sensing photoconductive mode feeding a transimpedance amplifier 402. Photodiode PD can be, for example, a model PIN-4.0-LLS, manufactured by UDT Sensors, Inc. Transimpedance amplifier 402 includes a resistor R, a capacitor C and an operation amplifier U, such as model ALD1701, manufactured by Advanced Linear Devices, Inc., Sunnyvale, Calif. Amplifier 402, including the RC circuit, performs low pass filtering and provides gain. It also serves as an antialiasing filter if A/D conversion is applied directly to its output 216. One of ordinary skill in the art will appreciate that a photodiode PD can alternatively be operated in a voltage sensing configuration. Further, one of ordinary skill in the art will appreciate that the use of other photodiodes (e.g., an avalanche photodiode) and other light detectors (e.g., a photoresistor, a photodarlington, a phototransistor), are within the spirit and scope of the present invention. One of ordinary skill in the art will also appreciate that other amplifier configurations (e.g., an integrator amplifier or a transistor based amplifier) can be used in place of transimpedance amplifier 402 shown in FIG. 4. An integrated photodiode/amplifier (e.g., a Burr-Brown OPT101, available from Burr-Brown Corporation, Tucson, Ariz.) can also be used.

In a conventional photoplethysmography device (e.g., 200B), a constant average optical power is delivered by light source 206 (e.g., an LED) and plethysmograph information (e.g., measurements of waveform 102 shown in FIG. 1) is determined based on time varying optical power incident on light detector 214. A photoplethysmography device can alternatively adjust the source of optical power such that a relatively constant average light intensity is detected at a light detector, as described in commonly assigned U.S. patent application Ser. No. 09/907,349 (Turcott), filed Jul. 16, 2001, entitled "Methods and Devices for Vascular Plethysmography Via Modulation of Source Intensity," which is incorporated herein by reference. The time-varying modulating signal (e.g., that controls the source power) can then be used as the plethysmography signal (i.e., the information signal), rather than the time-varying detected optical power. The time-varying detected optical power is used (e.g., in a feedback loop) to adjust the source intensity. Use of this alternative type of plethysmography device, in accordance with an embodiment of the present invention, shall be explained in more detail below with reference to FIG. 6.

B. Monitors for Assessing HF Status Based on Morphology of a Plethysmography Signal Referring back to FIG. 1, waveform 102 has a dicrotic pattern that is related to the dicrotic pattern typically exhibited by an arterial pressure waveform (not shown). Each period of an arterial pressure waveform, which looks very similar to waveform 102, includes a primary (i.e., larger) pulse also known as the systolic wave, and the second smaller pulse also known as the dicrotic wave. A dicrotic notch is located between the primary pulse and second pulse. In the article by Ewy et al., mentioned above, it was suggested that the level of the dicrotic notch decreases, the height of the dicrotic wave increases, and the area under the dicrotic wave increases in patients having severe impairment of myocardial function. The inventor of the present invention builds upon the teachings of the Ewy et al. article to assess the HF status of patients by measuring/monitoring the dicrotic characteristics of a plethysmography waveform (referred to herein interchangeably as a plethysmography signal). Stated another way, the inventor of the present invention has realized that the dicrotic characteristics of an arterial pressure waveform can be indirectly measured/ monitored using plethysmography. The inventor further realized that HF status can thus be assessed by measuring/ monitoring the morphology of plethysmography signals. As will be appreciated from the following description, there are many practical advantages to assessing HF status in accordance with this embodiment of the present invention.

In this embodiment of the present invention, changes in morphology of a pressure waveform are indirectly measured using an extravascular plethysmography device (e.g., a photoplethysmography device). Referring again to FIG. 1, the dicrotic character of plethysmography waveform 102 includes a primary pulse 112 followed by a secondary pulse 116 of smaller amplitude. A dicrotic notch 114 is located between each primary pulse 112 and secondary pulse 116.

Figure 5:
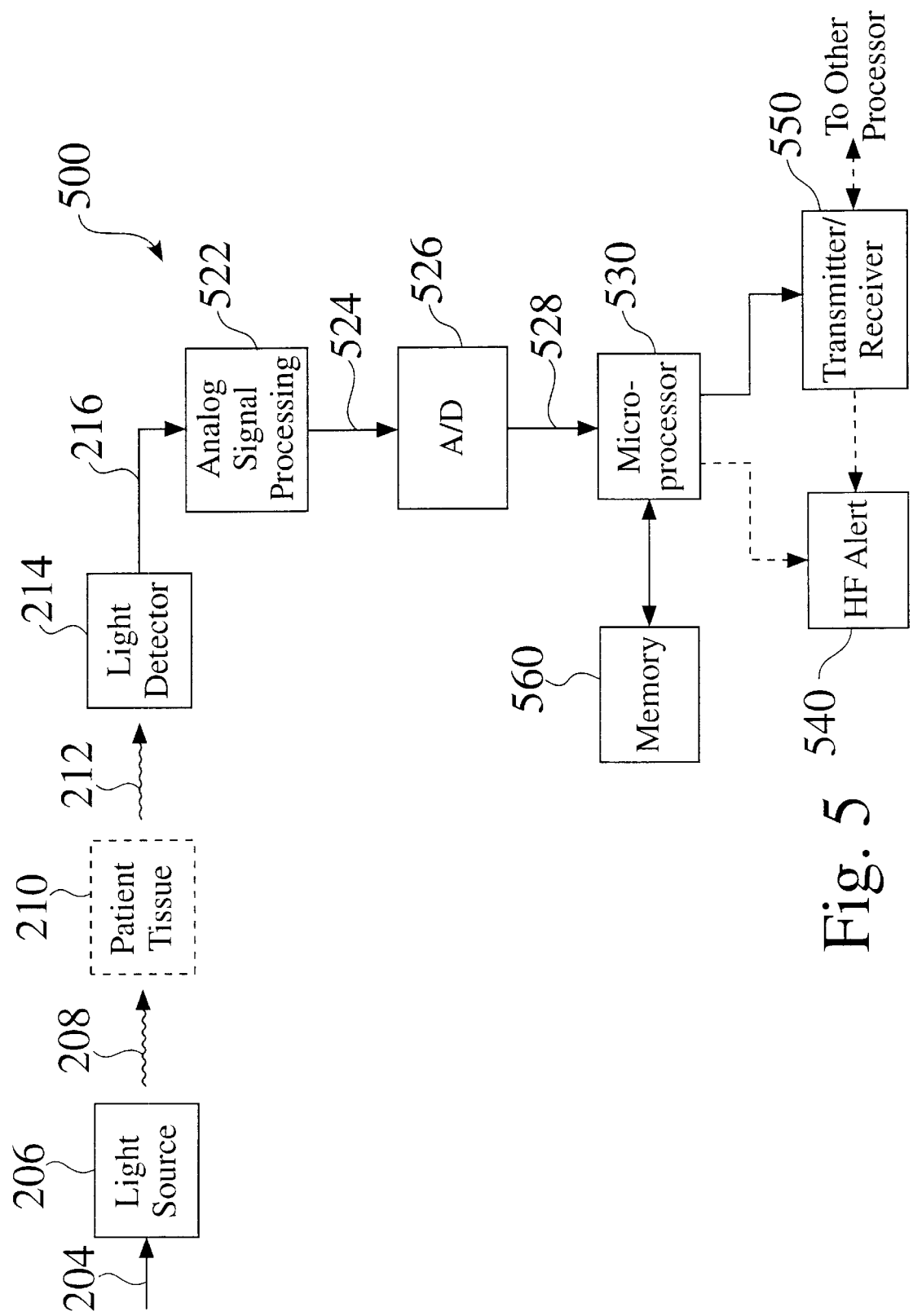
FIG. 5 illustrates an overview of a HF status monitor according to an embodiment of the present invention.

FIG. 5 includes a block diagram that provides an overview of a HF status monitor 500, according to an embodiment of the present invention. Light source 206 outputs a transmit light signal 208 of substantially constant average light intensity (as controlled by light control signal 204). Light signal 208 is transmitted through and/or reflected by (depending on the embodiment) patient tissue 210. Receive light signal 212 is received by light detector 214. Changes in light intensity of the received light signal 212 are proportional to changes in blood volume in patient tissue 210. Light detector 214 produces a light detection signal 216 that is representative of the received light signal 212. Analog output signal 216, which is an analog encoded information signal, is preferably filtered and amplified by analog signal processor block 522. A filtered and amplified signal 524 is then provided to an analog to digital converted (A/D) 526, which provides a digital encoded plethysmography information signal 528 to microprocessor 530.

Microprocessor 530 analyzes the encoded information signals 528. According to an embodiment of the present invention, microprocessor 530 analyzes the shape of the plethysmography signal represented by the encoded information signals 528. For example, microprocessor 530 can estimate arterial pulse amplitudes based on maximum and minimum values deciphered from the encoded information signals over durations of cardiac cycles.

If monitor 500 is not implanted, light source 206 and light detector 214 can be made small and can conveniently attach to a peripheral portion of the body, such as a finger, toe, or ear. Thus, patients are likely to tolerate regular use of these sensors for an extended period of time, such as during sleep each night. Particular embodiments include a finger cuff, a wristband, a configuration resembling a watch, and a configuration resembling a clip-on earring. Light source 206 and light detector 214 could be tethered to a larger unit containing the bulk of the electronic circuitry (e.g., microprocessor 530 and a memory 560). In this case, monitor 500 would be worn primarily when the patient is sleeping. Alternatively, data (e.g., from light detector 214, A/D 522, or microprocessor 530) could be continuously telemetered to a processor (e.g., microprocessor 530 or some other processor), which might be worn on the patient's clothing or located in the patient's home and/or office. In this case, the monitor could be worn both during sleep and during activity. Nevertheless, despite the cost advantages of an external embodiment, such an approach necessarily requires patient cooperation. Because of the disadvantages associated with this, as described above, a more preferred embodiment for monitor 500 is an implanted, extravascular configuration. However, it should be clear that many embodiments of the present invention are not limited to implantable implementations.

Monitor 500 can also include a transmitter/receiver 550 (i.e., a telemetric circuit) and a memory 560. If monitor 500 is chronically implanted, transmitter/receiver 550 enables the operating parameters of monitoring device 500 to be non-invasively programmed into the memory 560 through telemetric communications with an external device, such as a programmer or transtelephonic transceiver. Transmitter/ receiver 550, which is preferably controlled by microcontroller 530, also enables monitor 500 to communicate with other types of external processors. For example, transmitter/ receiver 550 enables plethysmography information (e.g., the values discussed above) and status information relating to the operation of device 500 (e.g., as contained in the microcontroller 530 or memory 560) to be sent to an external device (e.g., a remote processor or diagnostic system analyzer) through an established communication link. Microprocessor 530 can produce HF assessment information, and transmitter/receiver 550 can transmit the information to another processor as appropriate. Transmitter/receiver 550 can additionally, or alternatively, transmit measured values and/or calculated values to an external device (e.g., a remote processor) that can assess HF status based on such values. Alternatively, the encoded information signals (e.g., light detection signal 216) can be transmitted directly to an external device (e.g., a remote processor), and the external device can perform appropriate measurements and calculations (individually and collectively referred to herein as "determinations").

For examples of a transmitter/receiver 550 (also known as a telemetric circuit) of a chronically implantable device, see U.S. Pat. No. 4,809,697, entitled "Interactive Programming and Diagnostic System for use with Implantable Pacemaker" (Causey, III et al.), and U.S. Pat. No. 4,944,299, entitled "High Speed Digital Telemetry System for Implantable Device" (Silvian), each of which is hereby incorporated herein by reference. Another example of a telemetric circuit for use in a chronically implantable device is the TR1000 transceiver manufactured by RF Monolithics, Dallas, Tex. The TR 1000 is a single-chip, low-power, 916.5 MHz transceiver. The operating frequency of 916.5 MHz is desirable because of the modest requirements on antenna size it imposes. Additional implementation details relating to the TR 1000 is described in detail in commonly assigned U.S. patent application Ser. No. 09/438,017, entitled "Method for Monitoring Heart Failure," (Turcott) filed Nov. 11, 1999, which is incorporated herein by reference.

Monitor 500 can also include an HF alert block 540, that informs a patient, physician, clinician and/or any other person (or processor) of the HF status of the patient. If monitor 500 is implanted, HF alert block 540 is preferably an external device that telemetrically communicates with microprocessor 530 (e.g., using transmitter/receiver 550). HF alert 540 can include an indicator that provides, for example, an acoustic, mechanical vibration, optical and/or electrical indication and/or stimulation. Such an alert indicator can be triggered when a criterion (e.g., threshold) is satisfied (e.g., exceeded), as discussed below. In one embodiment HF alert 540 includes an inductive coil that generates both sound and mechanical vibration. In an alternative embodiment, the function of HF alert 540 is incorporated into microprocessor 530 and transmitter/receiver 550.

In monitor 500 described above, a relatively constant average optical power is delivered by light source 206 (e.g., an LED) and the plethysmograph signal is determined based on the time varying optical power incident on light detector 214. As previously mentioned, a photoplethysmography device can alternatively adjust the source of optical power such that a relatively constant average light intensity is detected at a light detector, as described in commonly assigned U.S. patent application Ser. No. 09/907,349, which has been incorporated herein by reference above. The time-varying modulating signal (e.g., that controls the source power) can then be used as the plethysmography signal (i.e., the information signal), rather than the time-varying detected optical power. The time-varying detected optical power is used (e.g., in a feedback loop) to adjust the source intensity. Use of this alternative type of plethysmography device, in accordance with an embodiment of the present invention, shall now be described with reference to FIG. 6.

Figure 6:
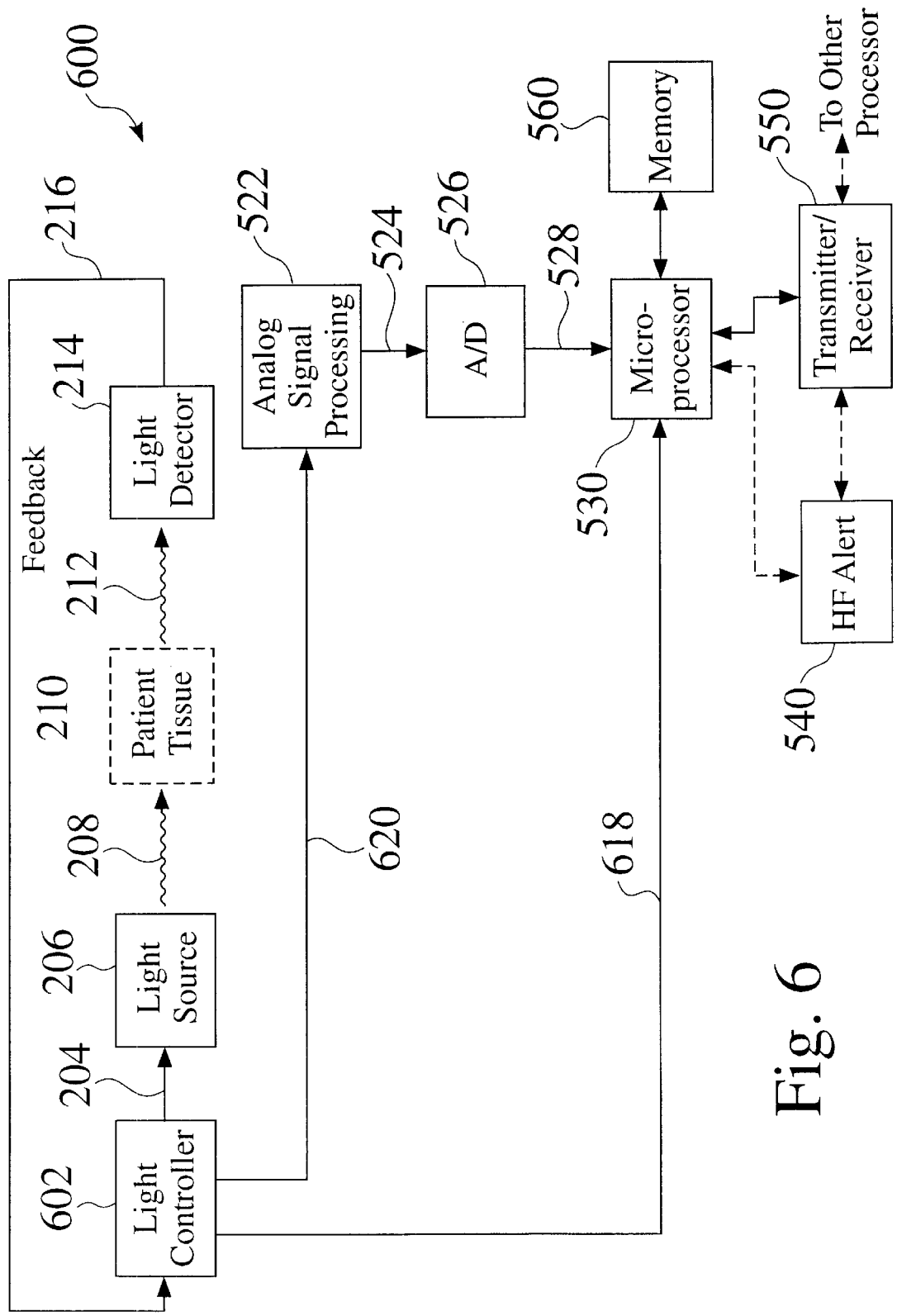
FIG. 6 illustrates an overview of a HF status monitor according to an alternative embodiment of the present invention.

Referring to FIG. 6, a monitor 600 includes a light controller 602 that produces light control signal 204 that drives light source 206. Light source 206 outputs a transmit light signal 208 based on light control signal 204. Light signal 208 is transmitted through and/or reflected by (depending on the embodiment) patient tissue 210. A receive light signal 212 is received by a light detector 214.

Light detector 214 provides light detection signal 216 (also referred to, for this embodiment, as feedback signal 216) to light controller 602. Light controller 602 adjusts light control signal 204, based on a difference between feedback signal 216 and an internal reference signal, such that a relatively constant average light intensity is detected by light detector 214. Stated another way, light controller 602 adjusts light control signal 204 based on a difference between feedback signal 216 and a reference signal, such that the difference between feedback signal 216 and the reference signal is minimized.

In this embodiment, a time-varying modulating signal of light controller 602 is used as (or to produce) the plethysmography signal (i.e., the information signal), rather than the time-varying detected optical power. For example, in one embodiment, described below with reference to FIGS. 6 and 7, an analog output signal 620 is provided from the light controller 602. Analog output signal 620, which is an analog encoded information signal, is preferably filtered and amplified by analog signal processor block 522. A filtered and amplified signal 524 is then provided to an analog to digital converted (A/D) 526, which provides a digital encoded information signal 528 to microprocessor 530. In an alternative embodiment, light controller 602 digitally controls light source 206, and a digital plethysmography information signal 618 is provided directly to microprocessor 530. Microprocessor 530 analyzes the encoded information signals (e.g., 618 or 528).

Figure 7:
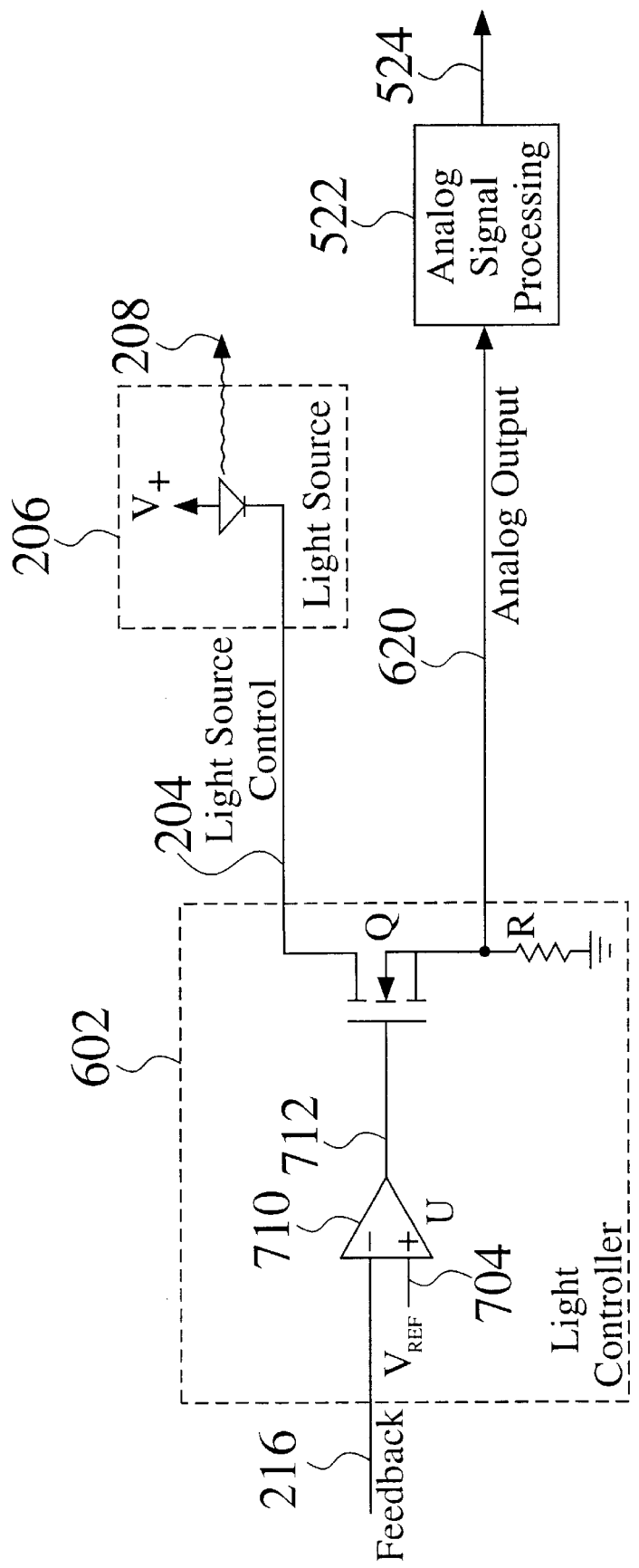
FIG. 7 illustrates a portion of the monitor of FIG. 6, according to an embodiment of the present invention.

Referring now to FIG. 7, light controller 602 outputs light control signal 204, which drives light source 206. In this embodiment, light control signal 204 is an analog voltage or current signal having a variable voltage or current amplitude. More specifically, in this embodiment the amplitude of the light control signal 204 is adjusted (i.e., increased or decreased) by light controller 602, based on a difference between feedback signal 216 and a reference signal 704 so that a relatively constant average light intensity is detected by light detector 214 (See FIG. 6). Stated another way, light controller 602 adjusts the amplitude of light control signal 204, based on a difference between feedback signal 216 and a reference signal, such that the difference between feedback signal 216 and the reference signal is minimized.

In this implementation, light controller 602 includes a comparator 710 (e.g., operation amplifier U), which compares feedback signal 216 to a fixed reference voltage signal 704 (e.g., 1.2 volts). The term "comparator" is used herein to refer to a device that performs a comparison between two input signals and generates an analog or digital (e.g., binary) output based on the results of the comparison. In this embodiment, comparator 710 produces an analog output 712 based on the comparison. Light controller 602 also includes a transistor Q (e.g., a MOSFET transistor as shown). Transistor Q is controlled by an output 712 (also referred to as comparison signal 712) of comparator 710. More specifically, transistor Q is turned on by an amount proportional to a difference between feedback signal 216 and fixed reference voltage signal 704. One of ordinary skill in the art will appreciate that various types of transistors, and/or various other types of current control circuits, can be used while still being within the spirit and scope of the present invention.

In this implementation, a modulated LED current, carrying the plethysmograph information, is sensed using a sense resistor R. More specifically, the information signal of interest, analog output 620 (which is the voltage across resistor R), is proportional to the LED current. As shown in FIG. 6, this signal 620 can be provided to analog signal processor 522, which filters and amplifies the signal. Filtered and amplified signal 524 can then be provided to A/D 526, which provides a digital encoded information signal 528 to microprocessor 530.

As mentioned above, alternatively and/or additionally, one or more digital output signals 618, which are digitally encoded information signals, are provided from light controller 602 to microprocessor 530. Additional details of such digital embodiments are described in U.S. patent application Ser. No. 09/907,349, which was incorporated herein by reference above.

Figure 8:
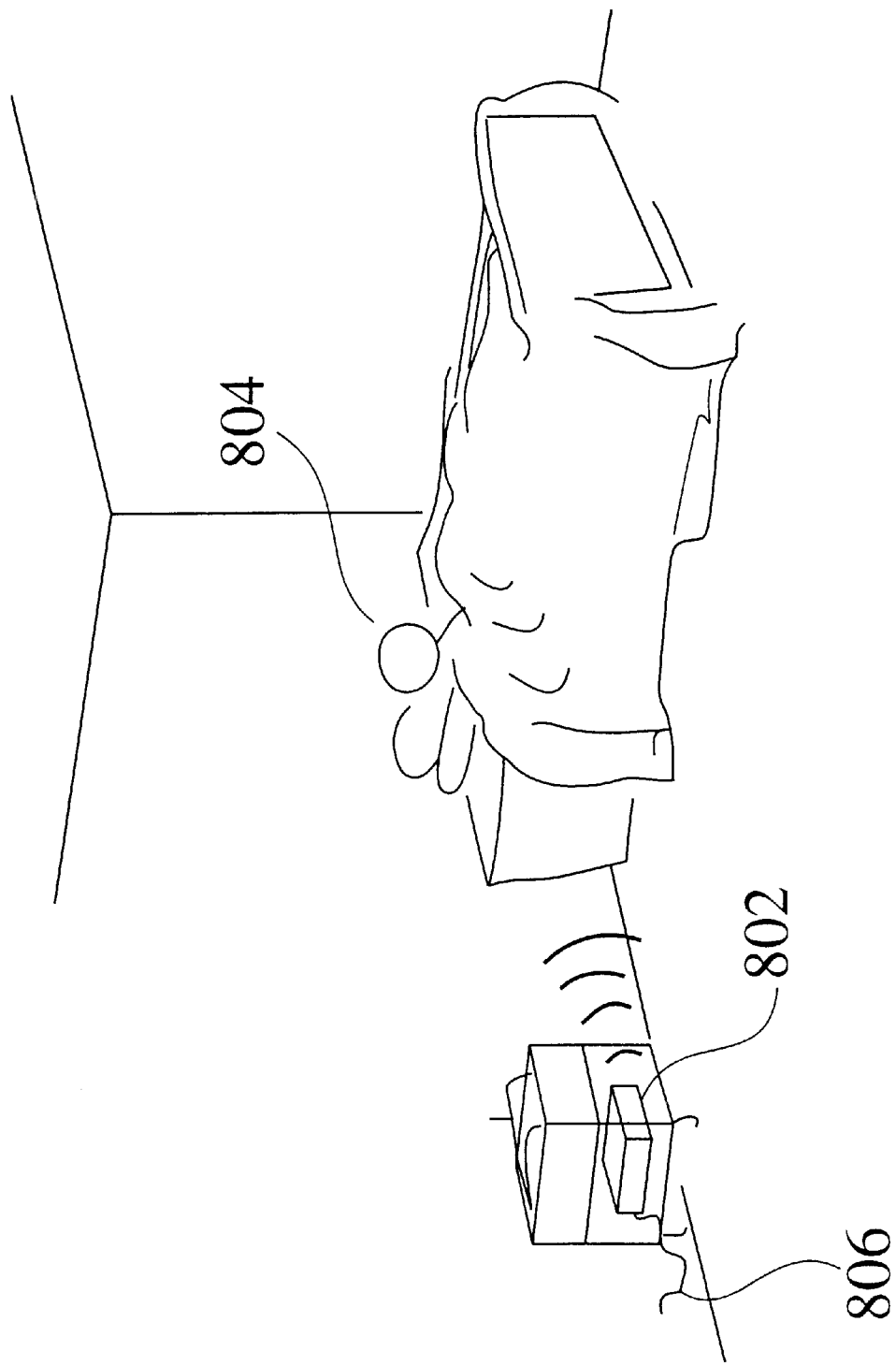
FIG. 8 illustrates the use of the telemetry-at-a-distance feature of the invention.

FIG. 8 illustrates placement of an external telemetry (i.e., transmitter/receiver) unit 802 in, for example, the patient's bedroom. External telemetry unit 802, using telemetry at a distance, allows the transfer of data to and from monitor 500 if it is a chronically implanted device or a device that clips on the finger, toe or earlobe, without the active participation of the patient 804 or a clinician. External telemetry unit 802 is preferably positioned in a location(s) regularly frequented by the patient, such as the patient's bedroom, office, and/or automobile. External telemetry unit 802 can be in communication (e.g., through a telephone line 806, network connection and/or wireless links) with a central location for further processing or review (e.g., by a clinician).

For each cardiac cycle microprocessor 530 can, for example, determine: maximum and minimum values of primary pulses 112, values of the dicrotic notches 114, and maximum values of secondary pulses 116. Microprocessor 530 can then, for example, produce averages of these values and perform calculations based on these values. Alternatively, microprocessor 530 can perform calculations based on each cardiac cycle of waveform 102, and then average the calculations as desired.

Figure 9:
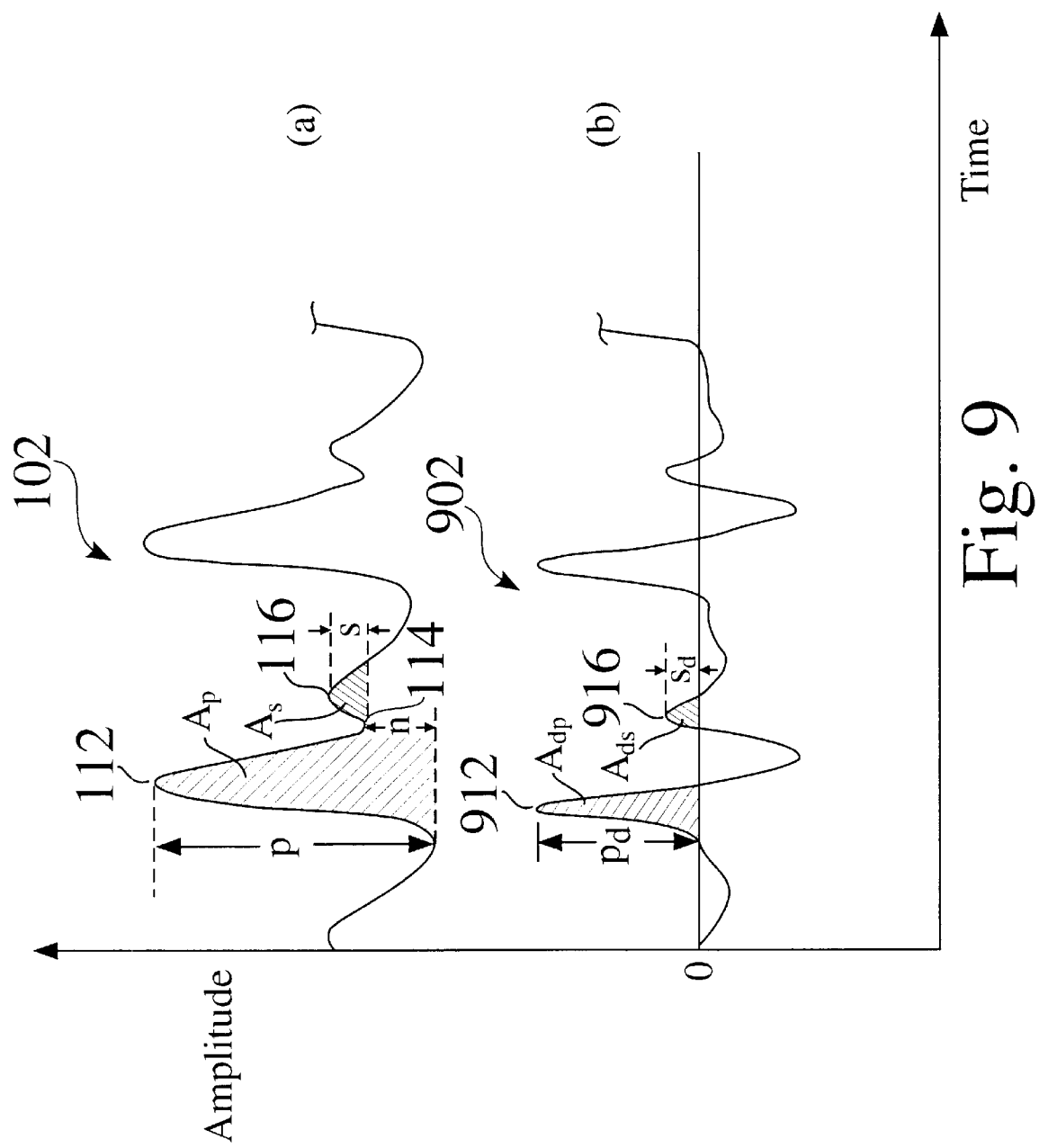
FIG. 9 is useful for illustrating determinations that can be produced from a plethysmography signal and/or a time derivative of the plethysmography signal.

Referring to waveform (a) of FIG. 9, microprocessor 530 can, for example, determine: [1] a peak height (p) of the primary pulse 112; [2] a level (n) of the dicrotic notch 114 above the foot (i.e., minimum value) of the primary pulse 112; and [3] a peak height of the secondary pulse 116.

From these values, microprocessor 330 can, for example, determine: [1] the dicrotic notch level (n) normalized by the primary pulse height (p) (i.e., n/p); [2] the height of the secondary pulse normalized by the primary pulse height (p) (i.e., s/p); [3] an estimated area ($A_p$) under the primary pulse 112; [4] an estimated area ($A_s$) under the secondary pulse 116 (above the dicrotic notch); and [5] the area under the secondary pulse as normalized by the area under the primary pulse (i.e., $A_s/A_p$). If desired, microprocessor 330 can use more than the maximum and minimum values of primary pulse 112, the value of the dicrotic notch 114, and the maximum value of secondary pulse 116, (i.e., use additional data points) to more accurately determine the area under the primary pulse 112 and secondary pulse 116. In addition, an estimate of the widths of the pulses can be used to further characterize the morphology of the waveform, or to further improve the estimate of other parameters, such as the areas. The pulse width can be estimated, for example, but measuring the width of each pulse at the level of the dicrotic notch, or at some specified level of the pulse, such as at half the maximum, or by measuring the time between the foot of the primary pulse and the dicrotic notch. If the signal is accoupled, that is, if the dc component has been removed from the signal, then the amplitudes of the primary and secondary pulses can be estimated from the peak values alone. One of ordinary skill in the art would understand how this can be accomplished.

Microprocessor 530 can then assess the HF status based on some or all of the above discussed values. Alternatively, the above discussed values can be transmitted to a remote processor (not shown) using transmitter/receiver 550. The remote processor can then assess the HF status based on some or all of the above discussed values. In an alternative embodiment, the encoded information signals (e.g., light detection signal 516) are transmitted directly to a remote processor (e.g., via transmitter/receiver 550), which can perform the functions of microprocessor 530. As will be described below, an HF alert 540 can be triggered if a predetermined criteria (e.g., threshold) is satisfied (e.g., exceeded). Various assessments of HF status based on such information are now discussed.

Secondary pulses 116 will become more prominent when heart failure exacerbation is developing. Accordingly, an assessment of HF status can be based on the pulse height (s) of secondary pulses 116. For example, alert indicator 540 can be triggered if the normalized secondary pulse height (s/p) exceeds a threshold. A threshold can be a predetermined value. Alternatively, a threshold can be dynamic in that its value is determined based on previously measured and/or calculated values. For example, alert indicator 540 can be triggered if the normalized height (s/p) increases by a certain percentage over previous values of the normalized height (s/p). Triggering of alert indicator 540 can indicate (e.g., to a patient, physician, clinician, monitoring staff, and/or monitoring computer) that a heart failure exacerbation (also known as, an episode of acute heart failure) is developing.

Alternatively, or additionally, the assessment of HF status can be based on the height (n) of the dicrotic notch (as normalized, i.e., n/p), which decreases when heart failure exacerbation is developing. Accordingly, alert indicator 540 can be triggered if the normalized height (n/p) of the dicrotic notch decreases below a threshold.

Alternatively, or additionally, the assessment of HF status can be based on the area ($A_s$) of the secondary pulse (as normalized, i.e., $A_s/A_p$), which similarly becomes more prominent when heart failure exacerbation is developing.

A common threshold can be used for many patients. Alternatively, thresholds can be patient specific.

Alternatively, or in addition to using threshold crossings as evidence of a heart failure exacerbation, an HF monitor (e.g., 500) of the present invention can look for a deviation away from a baseline. The monitor could continually update what it considers to be baseline, so that slow drifts do not trigger a warning, but rapid changes do. For example, a mean and standard deviation can be calculated for any of the above discussed values. If a newly determined value is different than a previously determined mean value by a specified multiple (e.g., 1.5 or 2) of the standard deviation, then an alert indicator can be triggered. The monitor could also consider deviations in either direction as evidence of an HF exacerbation.

Figure 10:
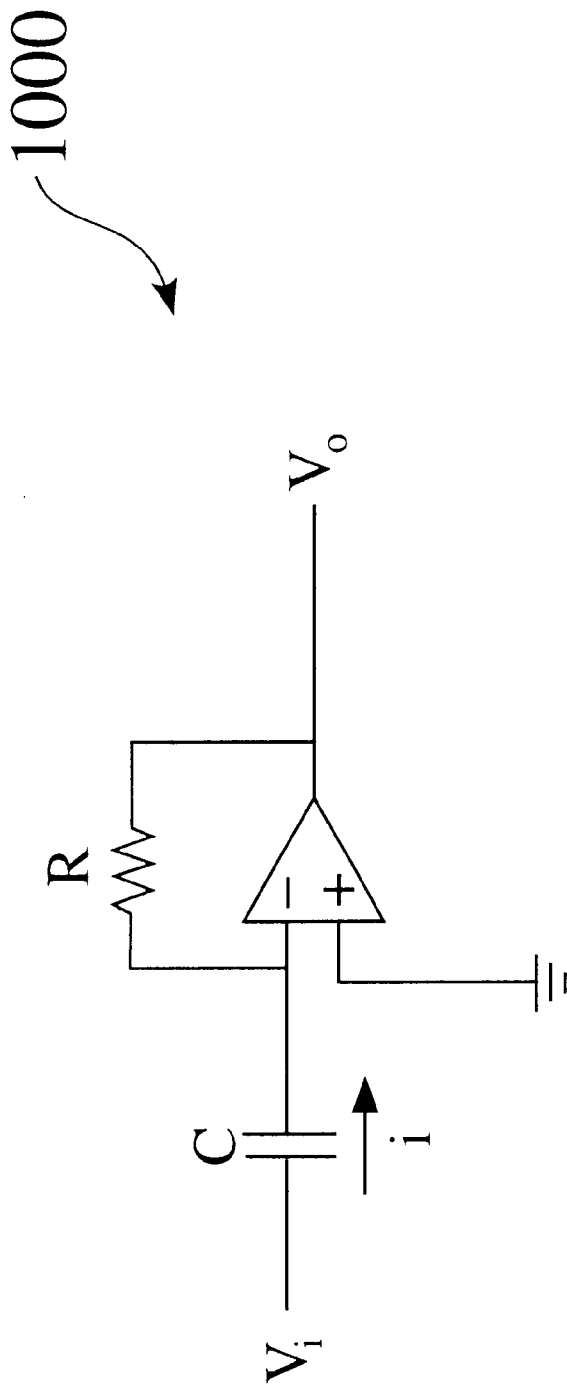
FIG. 10 illustrates an exemplary analog filter that can be used to produce the time derivative signal of FIG. 9, according to an embodiment of the present invention.

In alternative embodiments, HF assessment can be determined based on a time derivative of plethysmography signal 102. Still referring to FIG. 9, waveform (b) (i.e., signal 902) is the time derivative of waveform (a) (i.e., plethysmography signal 102). This waveform can be determined using an appropriate filter. An exemplary analog filter 1000 that can be used to produce time derivative signal 904, from plethysmography signal 102, is shown in FIG. 10 (where $V_i$ is plethysmography signal 102 and $V_o$ is time derivative signal 902). Alternatively, the time derivative of plethysmography signal 102 can be calculated numerically by, for example, microprocessor 530.

The time derivative of a signal represents the slope of the signal. Thus, as shown in waveform (b) of FIG. 9, the value of time derivative signal 902 equals zero at every maximum or minimum peak of plethysmography signal 102 shown in waveform (a). Thus, a significant advantage of using a time derivative signal (e.g., 902) to assess HF status is that it provides a zero reference point with multiple zero crossings. The time derivative signal (e.g., 902) can be used in conjunction with a plethysmography signal (e.g., 102) to locate the maximum peaks and minimum peaks (i.e., troughs) of the plethysmography signal. Alternatively, assessment of HF status can be determined directly from the time derivative signal (i.e., not in conjunction with the plethysmography signal 102).

Based on waveform (b), microprocessor 530 can, for example, determine: [1] a peak height ($p_d$) of primary derivative pulses 912 (above zero); and [2] a peak height ($s_d$) of the secondary derivative pulses 916 (i.e., the derivative of secondary pulses 116, not the second derivative of a pulse). Analog peak detectors, which are known in the art, can be used to detect these values. The values can then be provided by the peak detectors to microprocessor 530. Alternatively, these values can be determined in the digital domain by microprocessor 530.

From these values, microprocessor 530 can, determine: [1] the peak height ($s_d$) of the secondary derivative pulse 916 normalized by the total height of primary derivative pulse 912 ($p_d$) (i.e., $p_d/s_d$); [2] an estimated area ($A_{dp}$) under the primary derivative pulse 912; [3] an estimated area ($A_{ds}$) under the secondary derivative pulse 916 (above zero); and [4] the area under the secondary derivative pulse as normalized by the area under the primary pulse (i.e., $A_{ds}/A_{dp}$). If desired, microprocessor 530 can use more than the maximum values of primary derivative pulse 912 and secondary derivative pulse 916, to more accurately determine the areas under the pulses. The estimates of the areas of the primary derivative pulse and secondary derivative pulse can be improved by incorporating estimates of their widths. Widths can be measured at some specified level, e.g., their widths at half maximum. Alternatively, the times between successive zero crossings of the derivative signal 912 can be used to estimate the widths of the pulses. In a manner similar to that discussed above, microprocessor 530 can then assess the HF status based on some or all of the above discussed values.

Secondary derivative pulses 916 will become more prominent when heart failure exacerbation is developing. Accordingly, an assessment of HF status can be based on the pulse height ($s_d$) of secondary derivative pulses 916. For example, alert indicator 540 can be triggered if the normalized secondary derivative pulse height ($s_d/p_d$) exceeds a threshold. Alternatively, or additionally, the assessment of HF status can be based on the area ($A_{ds}$) of the secondary derivative pulses (as normalized, i.e., $A_{ds}/A_{dp}$), which similarly becomes more prominent when heart failure exacerbation is developing. For example, alert indicator 540 can be triggered if the normalized secondary derivative pulse area $A_{ds}/A_{dp}$ exceeds a threshold.

In another embodiment, HF status is assessed based on ejection time, $t_0$, which is the time required for the ventricles to eject blood. Surrogate measurements of ejection time can be made from a waveform representative of arterial pressure, possibly in conjunction with intracardiac electrogram or surface ECG. These surrogate measurements reflect the true ejection time, with the possible addition of an approximately constant delay. The delay is due to propagation of the arterial pressure wave from the heart to the location of the sensor at the periphery, and is present in the surrogate measurements when the onset of the measurement is defined by electrical activity of the heart. For example, referring to FIG. 11, ejection time surrogate $t_1$ is the time from electrical depolarization 1104 to dichrotic notch 114. Electrical depolarization can be detected, for example, based on a QRS complex of an intracardiac electrogram signal 1102 (shown in waveform (a)) or a surface ECG signal (not shown). In another embodiment, HF status can be assessed based on the time ($t_2$) from an electrical depolarization 1104 to the maximum point (i.e., peak) of the primary pulse 112. In still another embodiment, HF status is assessed based on the time ($t_3$) from electrical depolarization to the maximum of the time derivative waveform 902.

The pulse propagation delay in the ejection time surrogate measurements is avoided if the measurements are made exclusively from the morphology of the waveform, i.e., if electrical information is not used. For example, a surrogate measurement of the ejection time $t_4$ can be taken as the time from the beginning of an upstroke 1114 to the occurrence of the following dicrotic notch 1116. Using the plethysmography signal, this is the time from the absolute minimum to the time of the following dicrotic notch. Using the derivative signal, this is the time from the negative-to-positive zero crossing associated with a primary peak to the next negative-to-positive zero crossing. Alternatively, a surrogate measurement of the ejection time $t_5$ can be taken as the time from the beginning of an upstroke 1114 to the time of the primary peak 1118. Using the plethysmography signal, this is the time from the absolute minimum to the time of the absolute maximum. Using the derivative signal this is the time from the negative-to-positive zero crossing associated with a primary peak to the next positive-to-negative zero crossing.

The ejection time of a heart will vary in accordance with heart rate (HR). To account for the change in ejection time due to heart rate, the measured ejection time and ejection time surrogates can be adjusted in accordance with what is known as the ejection time index, as defined in an article by Weisler et al., entitled "Left ventricular ejection time index in man," *Journal of Applied Physiology*, Volume 18: pp. 919–923 (1963), which is incorporated herein by reference. More specifically, the adjusted ejection time=measured ejection time+(0.0016)*(HR). In other words, adjusted $t_0=t_0+$ 0.0016*HR. Similarly, the time $t_1$ from an electrical depolarization 1104 to the dicrotic notch 114, the time $t_2$ from an electrical depolarization 1104 to the maximum point of the secondary pulse 116, and the time $t_3$ from electrical depolarization 1104 to maximum of the time derivative waveform 902, should be adjusted based on HR if these times are used to assess HF status.

Figure 11:
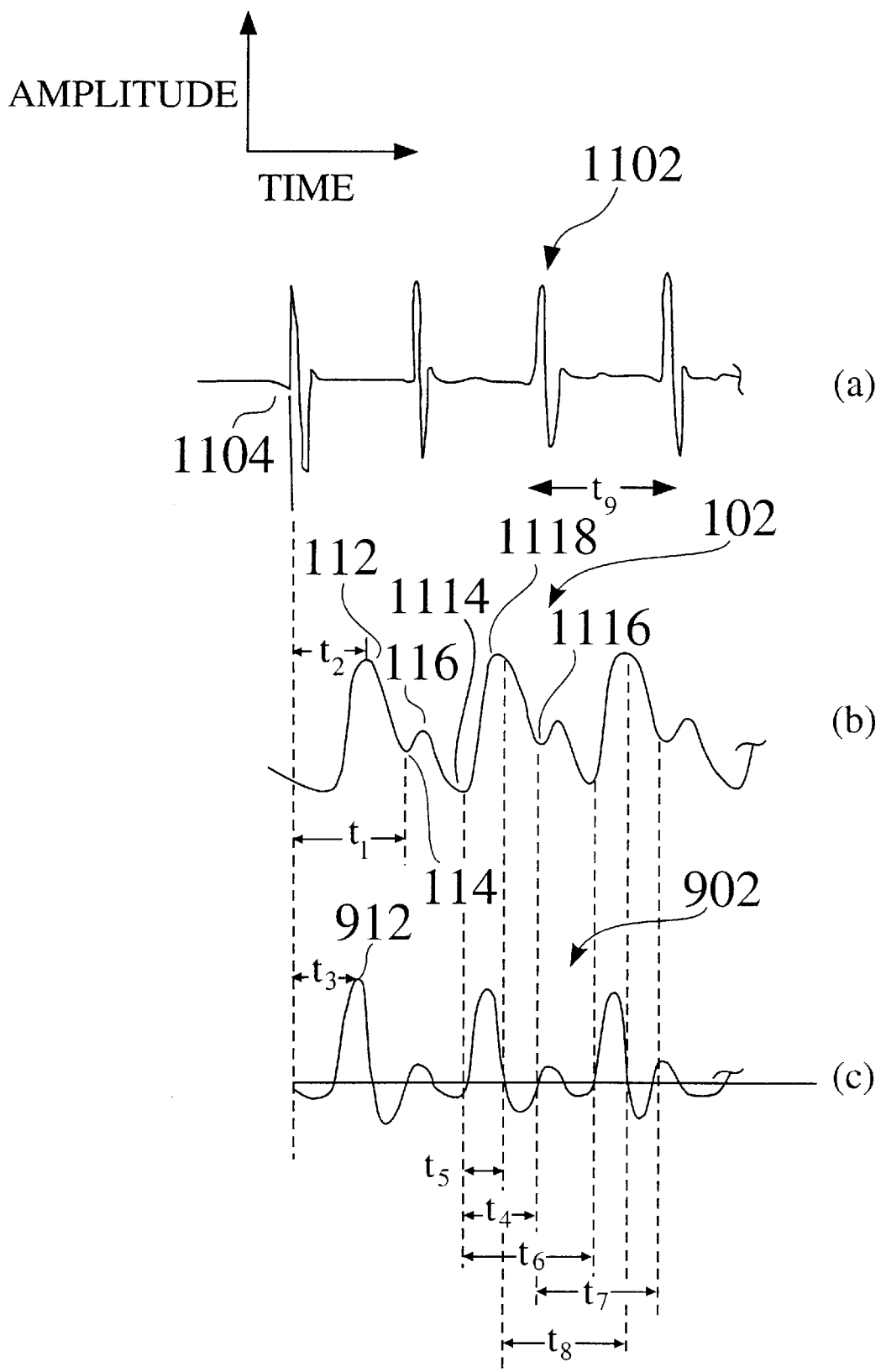
FIG. 11 is useful for illustrating determinations that can be produced from an electrogram signal and a plethysmography signal and/or a time derivative of the plethysmography signal.

Alternatively, these time measurements can be normalized by the cycle length of the heart, i.e., the time between successive heart beats. This is readily measured from the intracardiac electrogram or surface ECG as, for example, the time $t_9$ between successive QRS complexes. The same information can be obtained from the plethysmography signal, for example, as the time between every other dicrotic notch ($t_7$) or every other pre-primary-pulse minimum ($t_6$). As shown in FIG. 11, $t_9=t_6=t_7=t_8$. These can be measured directly from the derivative signal by recording the time between every other negative-to-positive zero crossing or every other positive-to-negative zero crossing. Thus, the cycle length is readily obtainable in a number of different ways, and can be used to normalize surrogate ejection time measurements to account for heart rate. For example, the ratio $t_4/t_6$ can be used as a surrogate for ejection time.

Each of the above discussed adjusted times (i.e., adjusted $t_0$, $t_1$, $t_2$ and $t_3$) will decrease when HF exacerbation is developing. This is likely due to an increase in sympathetic activity of the autonomic nervous system and an increase in circulating catacholamines (fight or flight response) that make the heart contract more vigorously. Accordingly, an alert indicator can be triggered if one or more of these times fall below a corresponding threshold(s). Such a threshold(s) can be static or dynamic. The threshold(s) can be the same for many patients, or specific to a patient.

Figure 12A:
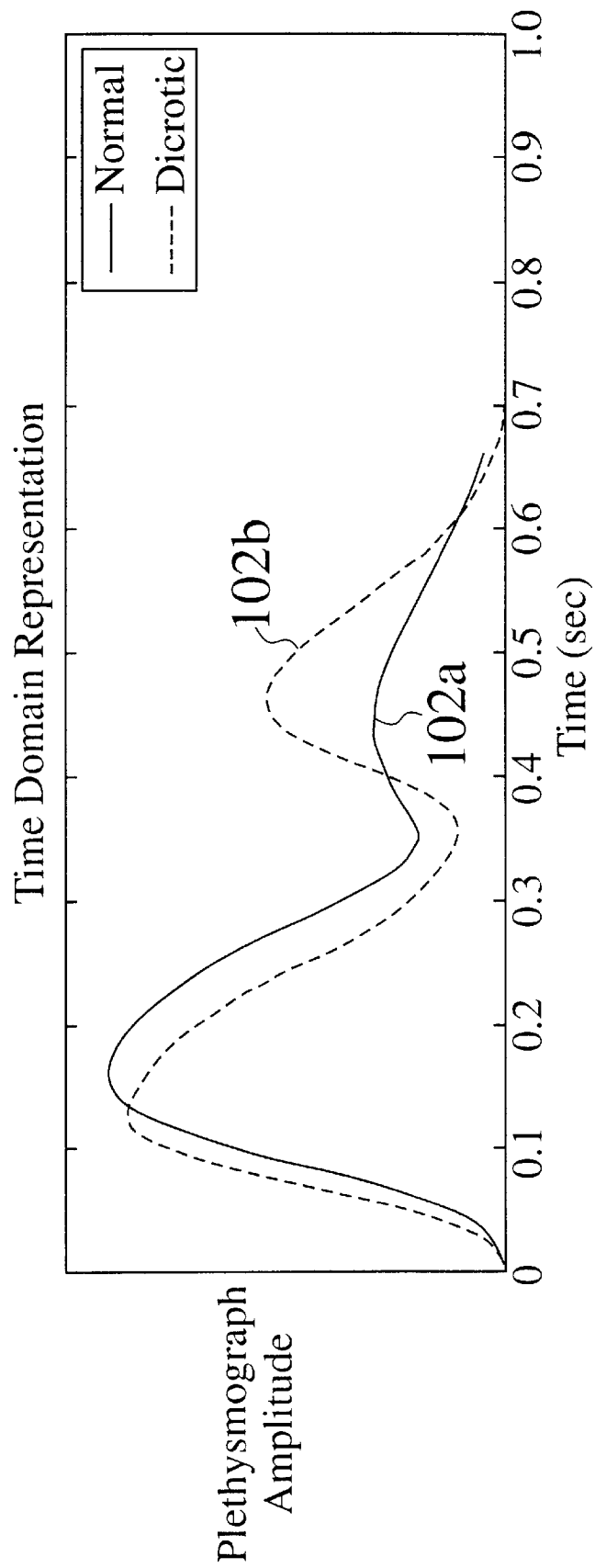
FIG. 12A illustrates exemplary plethysmography signals in the frequency domain.
Figure 12B:
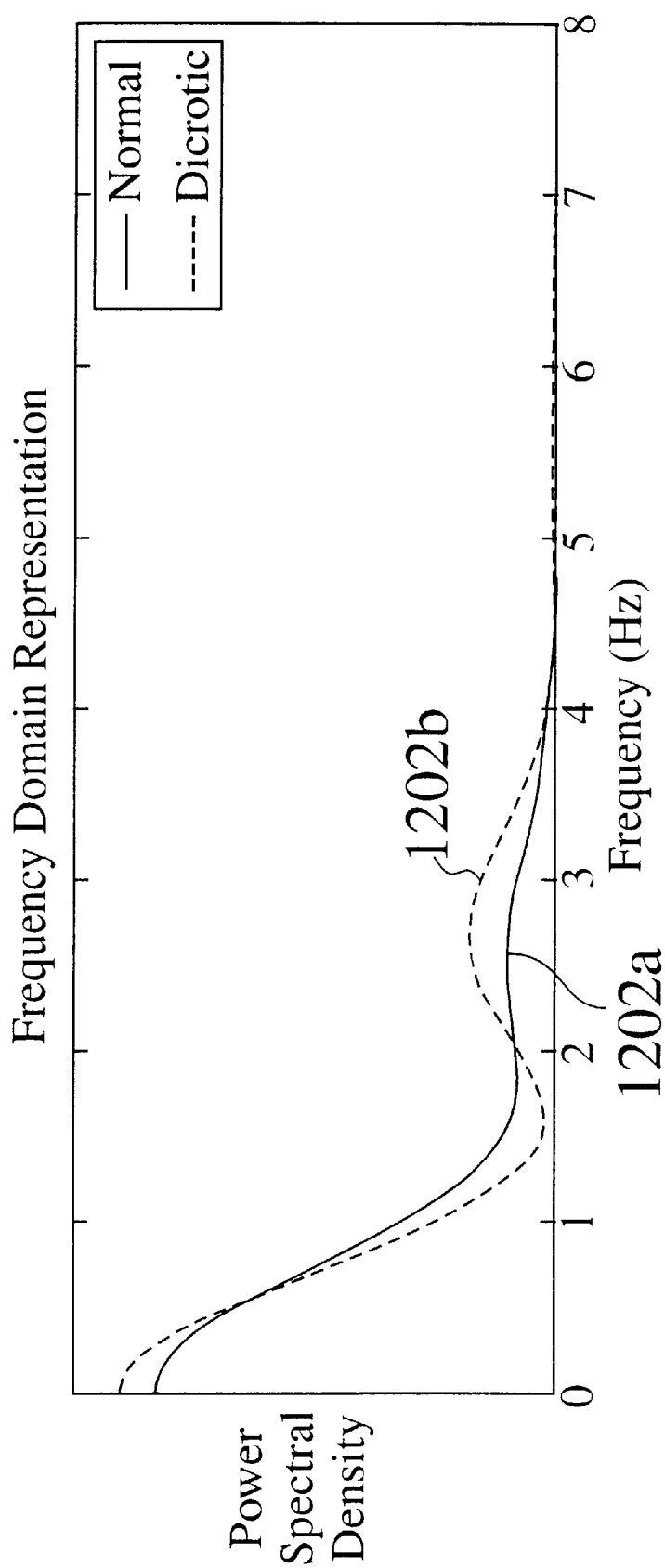
FIG. 12B illustrates frequency domain representations of the exemplary plethysmography signals shown in FIG. 12A.

In another embodiment, HF status can be assessed based on the frequency characteristics of a signal that is representative of arterial pulse pressure (e.g., plethysmography signal 102). This is because a signal representative of arterial pulse pressure should have relatively more high frequency power (i.e., more high frequency content) and relatively less low frequency power (i.e., less low frequency content) when heart failure exacerbation is developing. This is shown in FIGS. 12A and 12B. More specifically, the solid line 102a in FIG. 12A is a plethysmography signal (in the time domain) of a heart that is not experiencing HF exacerbation. The solid line 1602a in FIG. 12B is a frequency representation of plethysmography signal 102a. The dashed line 102b in FIG. 12A represents a corresponding plethysmography signal 102b when a HF exacerbation is developing. The dashed line 1202b in FIG. 12B is a frequency representation of plethysmography signal 102b. Notice the increase in high frequency content when HF exacerbation is developing.

In one embodiment, the frequency characteristics of a signal representative of arterial pulse pressure is determined by first high pass filtering this signal. A variance of the high pass filtered signal, which is representative of the high frequency power, is then determined. The variance is then compared to a threshold. An HF alert indicator can be triggered if the determined variance exceeds a threshold.

In another embodiment, the frequency spectrum of a signal representative of arterial pulse pressure is determined numerically. This can be accomplished, for example, using a Fast Fourier Transform (FFT) algorithm. The high frequency content can then be determined based on the frequency spectrum. This can be performed, for example, within microprocessor 530. An HF alert indicator can be triggered if the determined high frequency content exceeds a threshold.

Figure 13:
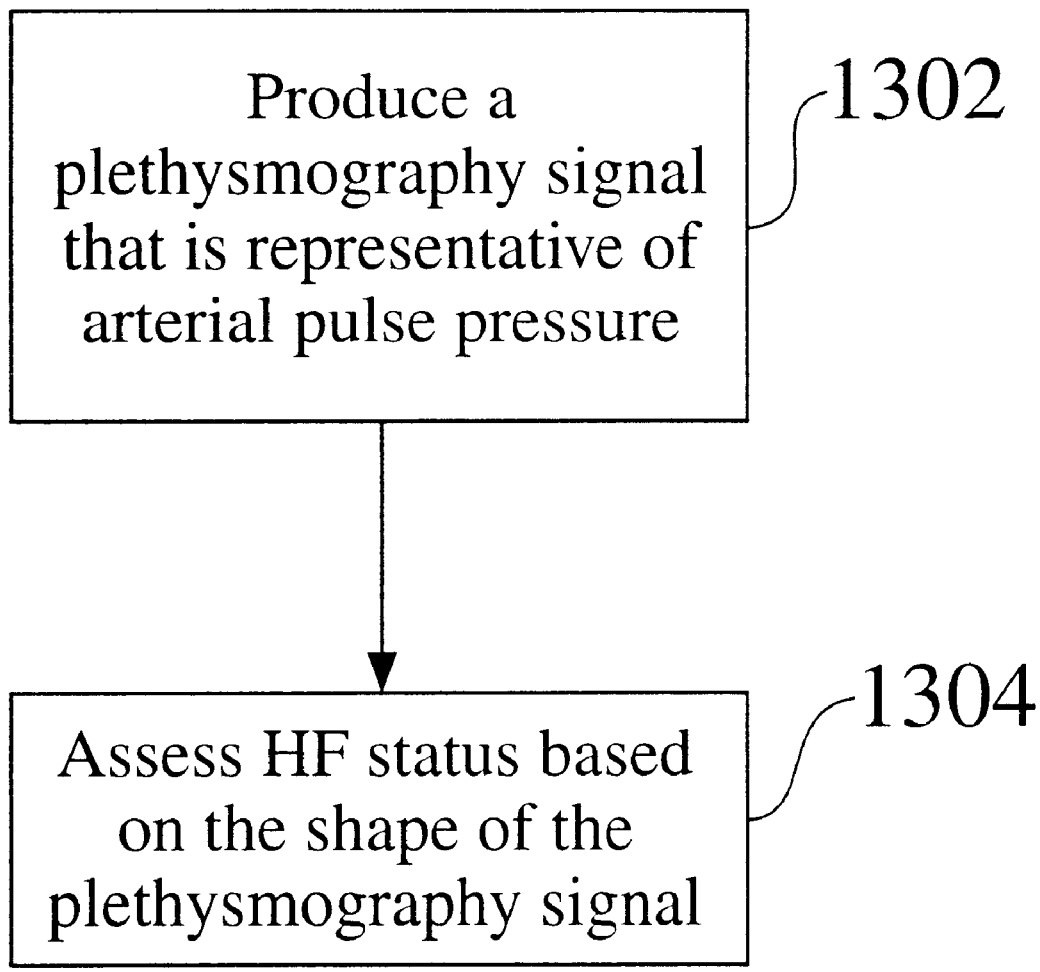
FIG. 13 is a flow diagram useful for describing an overview of the operation of various embodiments of the present invention that use a plethysmography signal to assess HF status.

FIG. 13 is a flow diagram that is useful for describing an overview of the operation of the above discussed embodiments of the present invention. At a first step 1302, a plethysmography signal that is representative of arterial pulse pressure is produced. At a next step 1304, HF status is assessed based on the shape (i.e., morphology) of the plethysmography signal.

Figure 14:
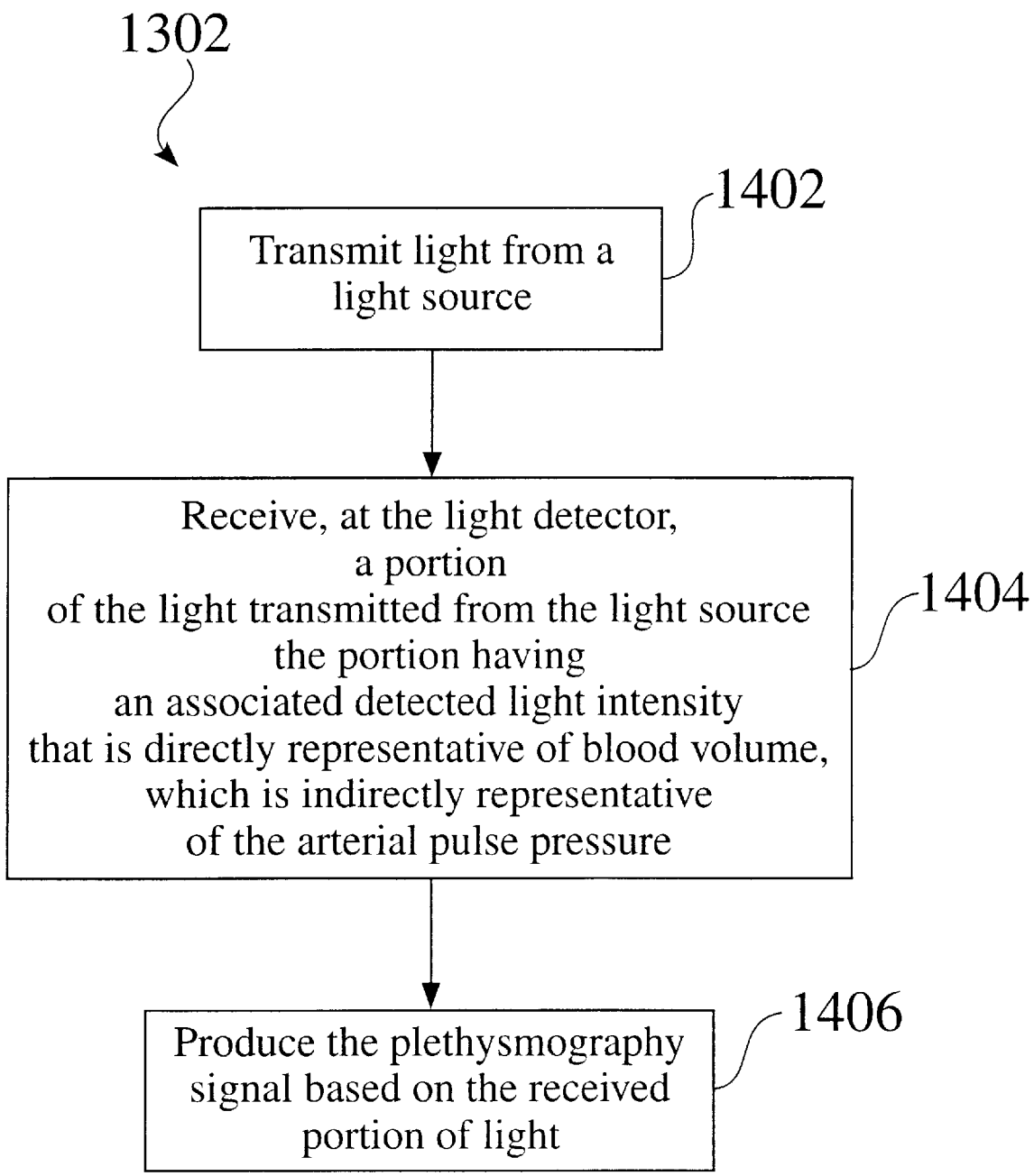
FIG. 14 is a flow diagram illustrating additional details of step 1302 of FIG. 13, according to an embodiment of the present invention.

FIG. 14 is a flow diagram illustrating details of step 1302, according to an embodiment of the present invention. At a first step 1402, light is transmitted from a light source (e.g., light source 206). At a next step 1404, a portion of the light transmitted from the light source is received at a light detector (e.g., light detector 214). The received portion of light, which was transmitted through a capillary bed (such as in an earlobe or finger tip or some other patient tissue) prior to being received at the light detector, has an associated detected light intensity. The light source and light detector, which can be arranged in a transmission configuration or a reflection configuration, can be incorporated in a chronically implanted device (e.g., as shown in FIG. 2C), or can be part of a non-implanted device (e.g., as shown in FIG. 2B). Next, at a step 1406, the plethysmography signal is produced based on the received portion of light.

Figure 15:
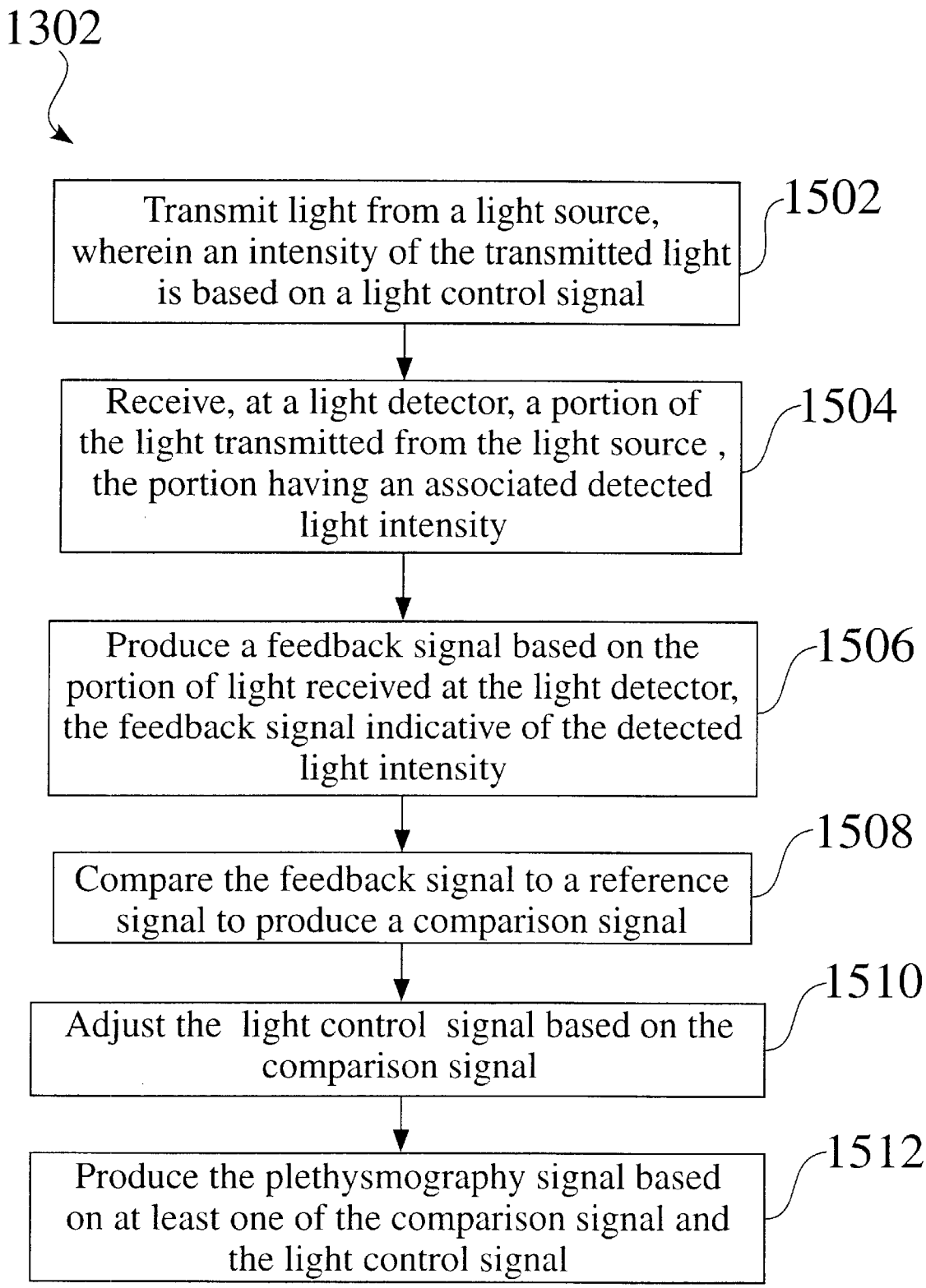
FIG. 15 is a flow diagram illustrating additional details of step 1302 of FIG. 13, according to an embodiment of the present invention.

FIG. 15 is a flow diagram illustrating details of step 1302, according to another embodiment of the present invention, where the time-varying modulating signal that controls the intensity of the transmitted light is used as (or to produce) the plethysmography signal, rather than the time-varying detected optical power. At a first step 1502, light is transmitted from a light source (e.g., light source 206), wherein an intensity of the transmitted light is based on a light control signal (e.g., 204). At a next step 1504, a portion of the transmitted light is received from the light source, at a light detector (e.g., light detector 214). The received portion of light, which was transmitted through a capillary bed (such as in an earlobe or finger tip or some other patient tissue) prior to being received at the light detector, has an associated detected light intensity. At a step 1506, a feedback signal (e.g., 216) is produced based on the portion of light received at the light detector. The feedback signal is indicative of the detected light intensity. At a step 1508, the feedback signal is compared to a reference signal (e.g., 704) to produce a comparison signal (e.g., 712). At a step 1510, the light control signal is adjusted based on the comparison signal. Finally, at a step 1512, the plethysmography signal is produced based on at least one of the comparison signal and the light control signal.

Additional details of step 1304, where HF status is assessed based on the shape of the plethysmography signal, shall now be discussed. As discussed above, this can be accomplished in many ways.

Figure 16:
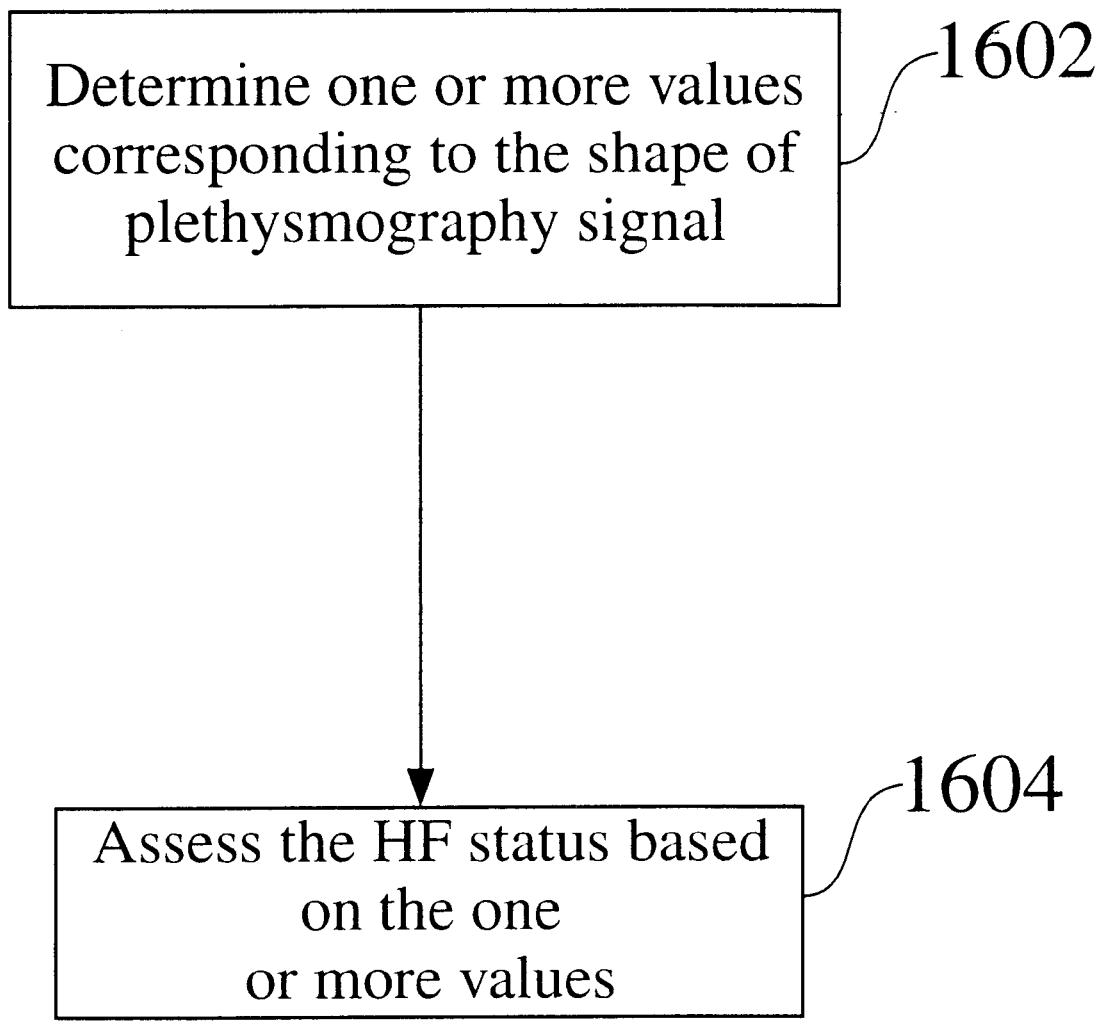
FIG. 16 is a flow diagram illustrating additional details of step 1304 of FIG. 13, according to an embodiment of the present invention.

FIG. 16 illustrates details of step 1304 according to an embodiment of the present invention. At a step 1602, one or more values corresponding to the shape of the plethysmography signal are determined. At a next step 1604, the HF status is assessed based on the one or more values determined at step 1602.

For example, step 1602 can include determining: a first value corresponding to the height of one or more primary pulses of the plethysmography signal; and a second value corresponding to the height of one or more secondary pulses of the plethysmography signal. The first value corresponds to total height (p) of the primary pulse 112, shown in FIG. 9. The second value corresponds to height (s) of secondary pulse 116, also shown in FIG. 9. Then, at step 1604, the HF status is assessed based on the first and second values. This step may include, for example, triggering an alert indicator (e.g., an alarm) based on the first and second values. For example, the alert indicator may be triggered if the normalized height (s/p) of the secondary pulses exceeds a threshold, as discussed above.

In another embodiment, step 1604 includes determining: a first value corresponding to the height of one or more primary pulses of the plethysmography signal; and a second value corresponding to the height of one or more dicrotic notches of the plethysmography signal. Then, at step 1604, the HF status is assessed based on the first and second values.

In another embodiment, step 1604 includes determining: a first value corresponding to an area under one or more primary pulses of the plethysmography signal; and a second value corresponding to the area under one or more secondary pulses of the plethysmography signal. Then, at step 1604, the HF status is assessed based on the first and second values.

In each of the above embodiments, an indicator alarm can be triggered based on the first and second values.

One of ordinary skill in the art will appreciate that similar flow charts could be used to illustrate many of the other embodiments of the present invention.

III. Chronically Implanted Sensor

The Ewy et al. article does not teach or suggest a chronically implanted sensor (defined herein as a sensor implanted for at least three days) that assesses HF status based on the shape of a signal that is representative of arterial pulse pressure. As described above, a plethysmography signal is an example of a signal that is representative of arterial pulse pressure. As also described above, there are many advantages to assessing HF status based on a plethysmography signal, which can be produced using an extravascular sensor. Thus, in an embodiment of the present invention, HF status is assessed based on the shape of a plethysmography signal produced by a chronic implanted plethysmography device (e.g., including light source 206 and light detector 214). Details of such an embodiment are described above.

In alternative embodiments of the present invention, HF status is assessed based on the shape of a signal, other than a plethysmography signal, that is representative of arterial pulse pressure. In each of these embodiments, the alternative signal representative of arterial pulse pressure is produced using a chronically implanted sensor that produces a signal having the desired dicrotic characteristics (i.e., a primary pulse, a dicrotic notch, and a secondary pulse).

For example, in an embodiment of the present invention an intra-arterial chronic pressure sensor is used to produce a signal that is representative of arterial pulse pressure. In order for the pressure sensor to produce a signal having the dicrotic characteristics that are necessary to assess HF status, the intra-arterial chronic pressure sensor should be implanted within an artery, such as the pulmonary artery. An example of an appropriate pressure sensor is the Medtronic Chronicle (also known as an "Implantable Hemodynamic Monitor"), which is manufactured by Medtronic, of Minneapolis, Minn. The Medtronic Chronicle is typically implanted in the right ventricle. While implanted in the right ventricle, the Medtronic Chronicle will not produce a signal having the desired dicrotic characteristics. In order for the Medtronic Chronicle to produce a signal that includes the desired dicrotic characteristics, the pressure transducer should be advanced from the right ventricle into the pulmonary artery. Other intra-arterial pressure transducers that can be used produce a signal that is representative of arterial pulse pressure, and include the desired dicrotic characteristics (so long as they are advanced into the pulmonary artery), are disclosed in U.S. Pat. No. 5,899,927, entitled "Detection of Pressure Waves Transmitted Through Catheter/Lead Body" (Ecker et al.), and U.S. Pat. No. 6,208,900, entitled "Method and Apparatus or Rate-Responsive Cardiac Pacing using Header Mounted Pressure Wave Transducer" (Ecker et al.), both of which are incorporated herein by reference.

Such alternative signals that are representative of arterial pulse pressure and include the desired dicrotic characteristics (e.g., a signal produced using the Medtronic Chronicle advanced into the pulmonary artery) will resemble a plethysmography signal (e.g., signal 102). Accordingly, the above described embodiments for assessing HF status based on the shape of a plethysmography signal can be used to assess HF status based on the shape of a signal representative of arterial pulse pressure that is produced using alternative chronically implanted sensors.

IV. Use of the Time Derivative of a Signal Representative of Arterial Pulse Pressure As described above, there are advantages to assessing HF status based on a time derivative of a signal representative of arterial pulse pressure. Although this was described above in the embodiments where the signal is a plethysmography signal, the same advantages exist if the signal representative of arterial pulse pressure is not a plethysmography signal, so long as the signal has the desired dicrotic characteristics (i.e., a primary pulse, a dicrotic notch, and a secondary pulse). Thus, assessment of HF status based on a time derivative of a signal representative of arterial pulse pressure is not limited to those embodiments where the signal is a plethysmography signal.

V. Analysis of Frequency Characteristics of a Signal Representative of Arterial Pulse Pressure As described above, HF status can be assessed based on the frequency characteristics of a signal representative of arterial pulse pressure. Although this was described above in the embodiments where the signal is a plethysmography signal, this aspect of the present invention can be used if the signal representative of arterial pulse pressure is not a plethysmography signal, so long as the signal has the desired dicrotic characteristics (i.e., a primary pulse, a dicrotic notch, and a secondary pulse). Thus, assessment of HF status based on the frequency characteristics of a signal representative of arterial pulse pressure is not limited to those embodiments where the signal is a plethysmography signal.

VI. Tailoring Drug Therapy

The above described embodiments of the present invention can be used to tailor drug therapy (e.g., beta blockers) that is used to treat HF. For example, the dosage of a drug can be adjusted based on the shape of a signal representative of arterial pulse pressure. More specifically, the shape of such a signal can be used as a quantitative measure of drug efficacy. Varying drug dosages can be administered over a period of time (e.g., multiple days or weeks). One or more signals representative of arterial pulse pressure can be measured for each dosage. These signals can then be analyzed in accordance with the various embodiments described above. Following the administration of such drug doses, and analysis of the respective signals representative of arterial pulse pressure, an optimum drug dosage can be determined based on the signals. This is just one example of how drug therapy can be tailored based on one or more signals representative of arterial pulse pressure.

VII. CONCLUSION

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. A method for assessing heart failure (HF) status of a patient, comprising the steps of:
    (a) producing a plethysmography signal that is representative of arterial pulse pressure; and
    (b) assessing HF status based on the frequency characteristics of the signal.

2. The method of claim 1, wherein step (b) further comprises tailoring drug therapy based on the frequency characteristics of the signal.

3. The method of claim 1, wherein step (b) includes performing a Fourier transform.

4. The method of claim 1, wherein step (b) includes high-pass filtering the signal.

5. A monitor for assessing heart failure (HF) status of a patient, comprising:
    a sensor to produce a plethysmography signal that is representative of arterial pulse pressure; and
    means for assessing HF status based on the frequency characteristics of the signal.

6. The monitor of claim 5, wherein the means for assessing HF status comprises a microprocessor.

7. The monitor of claim 6, wherein the means for assessing HF status comprises digital signal processing hardware.

8. The monitor of claim 5, further comprising an alert indicator to indicate that a HF exacerbation has been detected.

9. The monitor of claim 5, wherein the means for assessing HF status comprises a high-pass filter.

10. A method for assessing heart failure (HF) status of a patient, comprising the steps of:
    (a) producing a signal that is representative of arterial pulse pressure; and
    (b) assessing HF status based on the frequency characteristics of the signal by quantifying the high-frequency energy in the signal.

* * * * *